(12) United States Patent
Sliozberg et al.

(10) Patent No.: US 12,685,467 B2
(45) Date of Patent: *Jul. 21, 2026

(54) ANALYTE SENSOR AND METHOD FOR MANUFACTURING AN ANALYTE SENSOR

(71) Applicant: Roche Diabetes Care, Inc., Indianapolis, IN (US)

(72) Inventors: Kirill Sliozberg, Mannheim (DE); Alexander Steck, Hirschberg (DE)

(73) Assignee: Roche Diabetes Care, Inc., Indianapolis, IN (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/740,853

(22) Filed: Jun. 12, 2024

(65) Prior Publication Data

US 2024/0324918 A1 Oct. 3, 2024

Related U.S. Application Data

(63) Continuation of application No. PCT/US2022/080963, filed on Dec. 6, 2022.

(Continued)

(30) Foreign Application Priority Data

Jan. 18, 2022 (EP) ..................................... 22151916

(51) Int. Cl.
*A61B 5/1486* (2006.01)
(52) U.S. Cl.
CPC .... *A61B 5/14865* (2013.01); *A61B 2562/125* (2013.01)
(58) Field of Classification Search
CPC ......... G01N 27/30–301; G01N 27/307; G01N 27/327–3272; G01N 27/403
See application file for complete search history.

(56) References Cited

U.S. PATENT DOCUMENTS 6,144,871 A 11/2000 Saito et al.
2005/0013731 A1* 1/2005 Burke ................ G01N 27/3272
422/400

(Continued)

FOREIGN PATENT DOCUMENTS

EP 1801229 A1 6/2007
EP 3771413 A1 2/2021

(Continued)

OTHER PUBLICATIONS

Dawkins, Rebecca et al, A Screen-Printed Ag/AgCl Reference Electrode with Long-Term Stability for Electroanalytical Applications, Electrochimica Acta, vol. 393, p. 1-10, 2021.

(Continued)

*Primary Examiner* — James Lin
*Assistant Examiner* — Vivian A Tran

(57) ABSTRACT

The disclosure relates to an analyte sensor comprising a substrate, at least one working electrode, at least one second electrode and a membrane, wherein the membrane is located on top of the second electrode, and the second electrode has at least one first silver layer and at least one second silver layer which partially overlap with one another and have the same composition. The first and second silver layers intersect with one another to form a + or a T shape design. The sensor includes at least one exposed area of the first silver layer disposed on the exterior of the sensor to provide for direct contact with body fluid when implanted. The disclosure further relates to a process for manufacturing an analyte sensor.

19 Claims, 3 Drawing Sheets

Related U.S. Application Data

(60) Provisional application No. 63/293,729, filed on Dec. 24, 2021.

(56) References Cited

U.S. PATENT DOCUMENTS

| | | | |
|---|---|---|---|
| 2008/0242961 A1 | 10/2008 | Brister et al. | |
| 2010/0230285 A1* | 9/2010 | Hoss .................... | A61B 5/1473 |
| | | | 600/347 |
| 2021/0236028 A1* | 8/2021 | Mccanless ......... | A61B 5/14503 |

FOREIGN PATENT DOCUMENTS

| EP | 4115806 A1 | 1/2023 |
|---|---|---|
| WO | 2022008394 A1 | 1/2022 |

OTHER PUBLICATIONS

International Search Report and Written Opinion_PCT/US2022/080963, Mar. 28, 2023, pp. 1-19.

* cited by examiner

ANALYTE SENSOR AND METHOD FOR MANUFACTURING AN ANALYTE SENSOR

CLAIM OF PRIORITY

This application claims the benefit of International Application No. PCT/US2022/080963, which is entitled "ANALYTE SENSOR AND METHOD FOR MANUFACTURING AN ANALYTE SENSOR FIELD," and was filed on 6 Dec. 2022, the entire contents of which are hereby incorporated herein by reference. This application further claims the benefit of European Patent Application No. 22151916.8, which is entitled "ANALYTE SENSOR AND METHOD FOR MANUFACTURING AN ANALYTE SENSOR," and was filed on 18 Jan. 2022, the entire contents of which are hereby incorporated hereby reference. This application further claim the benefit of U.S. Provisional Patent Application No. 63/293,729, which is entitled "ANALYTE SENSOR AND METHOD FOR MANUFACTURING AN ANALYTE SENSOR," and was filed on 24 Dec. 2021, the entire contents of which are hereby incorporated by reference.

FIELD

The present disclosure relates to an analyte sensor comprising a substrate, at least one working electrode, at least one second electrode and a membrane, wherein the membrane is located on top of the at least one second electrode. The present disclosure further relates to a process for manufacturing the inventive analyte sensor as well as to an analyte sensor system comprising an analyte sensor according to the present disclosure and an electronics unit. The analyte sensor according to the present disclosure may mainly be used for conducting an analyte measurement in a body fluid of a user.

BACKGROUND

Biosensors for measuring analytes in biological fluids, in particular a sensor which is designed for implantation or subcutaneous insertion to measure body fluids, have to fulfill a variety of functions: on the one hand, the sensor must provide for specific and sensitive measurement without interference from e.g. particular components of body fluids. For this purpose, biosensors are frequently covered with membranes excluding particular compounds in order to allow access to the actual sensing sites only for low molecular weight compounds. While the specificity of biosensors is achieved by using biorecognition elements, such as enzymes, the sensitivity is often tailored by using diffusion limiting membranes. Finally, the implanted sensor must be biocompatible, where the inflammation reaction in the body is minimized, and for this purpose, an additional biocompatibility membrane may be applied.

Moreover, with implanted sensors, it is preferred to have sensors which can remain in place for a long period without deterioration of the measurement, in order to spare the patient frequently exchanging the sensor.

Implanted sensors, for example, comprise electrode systems which facilitate measurements of physiologically significant analytes such as, for example, like that of glucose in the patient's body. The working electrodes of such a sensor can have electrically conductive enzyme layers in which enzyme molecules are bound which release charge carriers by catalytic conversion of the analyte molecules. In this process, an electrical current is generated as a measuring signal whose amplitude correlates to the analyte concentration. These types of sensors are also called electrochemical sensors.

Biosensors that detect analytes via electrical signals, such as current (amperometric biosensors) or charge (coulometric biosensors), are of special interest because electron transfer is involved in the biochemical reactions of many important bioanalytes. For example, the reaction of glucose with glucose oxidase involves electron transfer from glucose to the enzyme to produce gluconolactone and reduced enzyme. In an example of an amperometric glucose biosensor, glucose is oxidized by oxygen in the body fluid via a glucose oxidase-catalyzed reaction that generates gluconolactone and hydrogen peroxide, and the hydrogen peroxide is electrooxidized and correlated to the concentration of glucose in the body fluid.

Some biosensors are designed for implantation in a living animal body, such as a mammalian or a human body, merely by way of example. Typically, such biosensors have a three-electrode system provided with working electrodes which sensitively respond to species of interest, reference electrodes which control the potentials of working electrodes, and counter electrodes which pass the electrical currents generated on the working electrodes. Alternatively, the reference and counter electrodes can be combined as one electrode to form a two-electrode system. The working electrode is typically constructed of a sensing layer, which is in direct contact with the conductive material of the electrode, and a diffusion-limiting membrane layer on top of the sensing layer. The reference electrode is typically composed of Ag/AgCl, which is fabricated via screen printing or electroplating. However, the lifetime of a screen-printed Ag/AgCl reference electrode is typically limited in an in vivo amperometric sensor due to degradation of the AgCl and potential leaching thereof into the surrounding tissue.

As a result, the sensor's life as a whole is often limited by the amount of Ag/AgCl available on the sensor's reference electrode. Although increasing the level of Ag/AgCl loaded on the reference electrode can prolong the lifetime of the reference electrode, the small and compact size of an implantable biosensor presents limitations in doing so.

U.S. Pat. No. 9,895,091B2 discloses electrochemical sensors. These electrochemical sensors can comprise an impermeable dielectric layer on top of Ag/AgCl of a reference electrode. This coating is used to extend the reference electrode's lifetime. The electrochemical sensor disclosed has a layered structure wherein the reference electrode is positioned on top of a working electrode. The working electrode is separated from the reference electrode by an insulating layer.

U.S. Pat. No. 10,470,691B2 discloses an analyte sensor which comprises a working electrode and a reference electrode. The sensor may comprise an insulator formed of an insulating material. A portion of the insulator may be removed to expose the working electrode and/or the reference electrode.

WO2017/106411A1 discloses an electrode for transdermal electrical stimulation where the electrode comprises a substrate and a multi-layered active region, where an improved charge distribution is realized in a multi-layer electrode design.

The manufacturing of the sensors disclosed in the prior art is very time- and cost-consuming. Further, they have drawbacks with regard to their long-term stability. Also, in two-electrode sensors having a combined counter electrode/reference electrode and comprising Ag/AgCl electrode areas, it has been important to have a controlled formation of the exposed Ag/AgCl areas (such areas are needed for mass transfer) to provide for the above-described second electrochemical half-reaction in a non-limiting way. This half-reaction involves a reduction of ionic silver from AgCl to an elemental silver (Ag). Thus, for each Ag+ ion reduced, one electron is consumed to form one atom of elemental silver. The electrons consumed in this half-reaction are generated during the analyte (e.g., glucose) oxidation reaction, and these electrons must find an acceptor with high kinetics so that the reduction half-reaction will not be limiting and the analyte (e.g., glucose) oxidation reaction will take place quantitatively. Therefore, the exposed area(s) must be sufficiently large, to not make the analyte detection reaction at the working electrode limited by the counter-reaction. On the other hand, too much exposed AgCl can lead to biocompatibility problems and a few other issues. One issue is that maintaining such small surface area(s) of the exposed Ag/AgCl demands correspondingly precise manufacturing methods.

It is therefore desirable to provide an analyte sensor which avoids at least in part certain drawbacks of the prior art, in particular with regard to its manufacturability and also with regard to its long-term stability and good performance in use.

European Patent Application No. 21183849.5, filed Jul. 6, 2021, discloses analyte sensors which enjoy many advantages over the prior art sensors. Such sensors include at least one second electrode comprising first and second silver layers which partially overlap and have different compositions.

SUMMARY

This section provides a general summary of the disclosure, and is not a comprehensive disclosure of its full scope or all of its features. Further areas of applicability and aspects of the invention will become apparent from the claims, the figures and the description provided herein. The description in this summary is intended for purposes of illustration only and is not intended to limit the scope of the present disclosure.

At least one of the above-described issues/problems is solved by an analyte sensor according to independent claim 1 as well as by the method for manufacturing a sensor according to independent claim 14 and by the analyte sensor system according to independent claim 19. Preferred embodiments of the invention which may be realized in an isolated way or in any arbitrary combination are disclosed in the dependent claims and throughout the specification and the figures.

The inventive analyte sensor is particularly easy to manufacture. It furthermore exhibits an excellent long-term stability and a stable sensitivity. In particular, the inventive analyte sensor allows the analyte sensor to comprise only two electrodes instead of three, which makes the inventive analyte sensor particularly cost-efficient. Further, it has an improved biocompatibility.

As used in the following, the terms "have", "comprise", or "include" or any arbitrary grammatical variations thereof are used in an exclusive way. Thus, these terms may both refer to a situation in which, besides the feature introduced by these terms, no further features are present in the entity described in this context and to a situation in which one or more further features are present. As an example, the expressions "A has B", "A comprises B" and "A includes B" may both refer to a situation in which, besides B, no other element is present in A (i. e. a situation in which A solely and exclusively consists of B) and to a situation in which, besides B, one or more further elements are present in entity A, such as element C, elements C and D or even further elements.

Further, it should be noted that the terms "at least one", "one or more" or similar expressions indicating that a feature or element may be present once or more than once typically will be used only once when introducing the respective feature or element. In the following, in most cases, when referring to the respective feature or element, the expressions "at least one" or "one or more" will not be repeated, notwithstanding the fact that the respective feature or element may be present once or more than once.

Further, as used in the following, the terms "preferably", "more preferably", "particularly", "more particularly", "specifically", "more specifically" or similar terms are used in conjunction with optional features, without restricting alternative possibilities. Thus, features introduced by these terms are optional features and are not intended to restrict the scope of the claims in any way. The invention may, as the skilled person will recognize, be performed by using alternative features. Similarly, features introduced by "in an embodiment of the invention" or similar expressions are intended to be optional features, without any restrictions regarding alternative embodiments of the invention, without any restrictions regarding the scope of the invention and without any restrictions regarding the possibility of combining the features introduced in such way with the optional or nonfunctional features of the invention.

A first aspect of the present invention relates to an analyte sensor which comprises a substrate comprising a first side and a second side;

at least one working electrode positioned on the first side of the substrate, the at least one working electrode comprising at least one electrically conductive material;

at least one second electrode positioned on the second side of the substrate, the at least one second electrode comprising at least one first silver layer and at least one second silver layer, wherein the second silver layer partially overlaps with the first silver layer, wherein the first and second silver layers comprise the same composition; and a membrane comprising a polymer composition which comprises a hydrophobic polymer, wherein the membrane is located on top of the at least one second electrode, wherein the sensor comprises at least one exposed area of the first silver layer, said at least one exposed area being disposed on the exterior of the sensor and configured to be in direct contact with body fluid when the sensor is implanted in a user.

In another aspect of the present invention, a method is provided for manufacturing an analyte sensor, in particular the inventive analyte sensor, the method comprising the steps:

a) providing a raw substrate which comprises a first side and a second side;

b) preparing a working electrode region on the first side of the raw substrate, the preparing of the working electrode region comprising the steps:

b1) applying an electrically conductive material to the first side of the raw substrate, b2) applying a sensing material at least partially on the electrically conductive material;

c) preparing a second electrode region on the second side of the raw substrate, the preparing of the second electrode region comprising the steps:

c1) applying a first silver composition to form a first silver composition region on the second side of the raw substrate, c2) applying a second silver composition as a plurality of separated second silver composition regions on the second side of the raw substrate, wherein the second silver composition has the same composition as the first silver composition and wherein the second silver composition is applied over the first silver composition such that the second silver composition regions partially overlap with the first silver composition region or the first silver composition is applied over the second silver composition so that the first silver composition region partially overlaps with the second silver composition regions;

d) applying a polymer composition on top of the second electrode region, to obtain a membrane, wherein the polymer composition comprises a hydrophobic polymer; and e) cutting the raw substrate, the working electrode region, the second electrode region and the membrane, wherein only the first silver composition region of the second electrode region is cut such that the first silver composition region comprises at least one exposed area configured to be in direct contact with body fluid when the sensor is implanted in a user.

The term "analyte sensor" within the context of the present invention may refer to any device being configured for the detection of an analyte.

The term "analyte" may refer to any arbitrary element, component or compound which may be present in a body fluid and the concentration of which may be of interest for the user. Preferably, the analyte may be or may comprise an arbitrary chemical substance or chemical compound which may take part in the metabolism of the user, such as at least one metabolite. As an example, the analyte may be selected from the group consisting of glucose, cholesterol, triglycerides, and lactate. Additionally or alternatively, however, other types of analytes and/or any combination of analytes may be determined. Preferably, the analyte is glucose.

Thus, the analyte sensor is preferably a biosensor. Further preferably, the analyte sensor is an electrochemical sensor. The term "electrochemical sensor" refers to a sensor which is adapted for performing at least one electrochemical measurement, in particular, a plurality or series of electrochemical measurements, in order to detect the analyte comprised within the body fluid by using an amperometric method. Especially, the term "electrochemical measurement" refers to the detection of an electrochemically detectable property of the analyte, such as an electrochemical detection reaction, by employing amperometric methods. Thus, for example, the electrochemical detection may be carried out by applying and comparing one or more electrical potentials. Specifically, the electrochemical sensor may be adapted to generate at least one electrical measurement signal which may directly or indirectly indicate the presence and/or absence of the electrochemical detection reaction, such as at least one current signal and/or at least one voltage signal. The measurement may be a quantitative and/or a qualitative measurement.

In a particularly preferred embodiment of the present invention, the analyte sensor may be fully or partially implantable and may, thus, be adapted for performing the detection of the analyte in the body fluid in the subcutaneous tissue, in particular, an interstitial fluid. As used herein the terms "implantable" or "subcutaneous" refer to be fully or at least partially arranged within the body tissue of the user, preferably partially arranged within the body tissue of the user. For this purpose, the analyte sensor may comprise an insertable portion, wherein the term "insertable portion" may generally refer to a part or component of an element configured to be insertable into an arbitrary body tissue, preferably the skin, while other parts or components may remain outside of the body tissue. Preferably, the insertable portion may fully or partially comprise a biocompatible membrane, i.e., a surface which may have as little detrimental effects on the user, the patient, or the body tissue as possible, at least during typical durations of use.

Thus, preferably, the analyte sensor of the present invention is an implantable sensor.

As generally used, the term "body fluid" may refer to fluid, in particular liquid, which may typically be present in a body or a body tissue of the user or the patient and/or which may be produced by the body of the user or the patient. Preferably, the body fluid may be selected from the group consisting of blood and interstitial fluid. However, additionally or alternatively, one or more other types of body fluid may be used, such as saliva, tear fluid, urine or other body fluids. During the detection of the analyte, the body fluid may be present within the body or body tissue. Thus, the analyte sensor may be configured for detecting the analyte within the body tissue. The analyte sensor is in one embodiment suitable for short-term application, e. g. 3 to 21 days, preferably 7 to 21 days, preferably 14 to 21 days, or for long-term application e. g. 1 to 12 months. During its application, the analyte may be determined by continuous or discontinuous measurements.

The analyte sensor of the invention is an electrochemical sensor comprising at least one working electrode and at least one second electrode. More particularly, the sensor is an amperometric electrochemical sensor comprising the at least one working electrode and the at least one second electrode. The working electrode is sensitive for the analyte to be measured at a polarization voltage which may be applied between the at least one working electrode and the at least one second electrode and which may be regulated by a potentiostat. A measurement signal may be provided as an electric current between the at least one working electrode and the at least one second electrode.

The inventive analyte sensor comprises a substrate which comprises a first side and a second side.

Within the context of the present invention, the term "substrate" specifically may refer, without limitation, to any kind of material or combination of materials which is suitable to form a carrier layer to support the at least one working electrode and the at least one second electrode. In particular the substrate may comprise an electrically insulating material. Within the context of the present invention "electrically insulating material" is a broad term and given its ordinary and customary meaning to a person of ordinary skill in the art. The term "electrically insulating material" may also encompass a dielectric material. The term specifically may refer, without limitation, to a material or combination of materials which prevent the transfer of electrical charges and which do not sustain a significant electrical current. Specifically, without limiting other possibilities, the at least one electrically insulating material may be or may comprise at least one insulating resin such as insulating epoxy resins used in manufacturing of electronic printed circuit boards. In particular, it may comprise or be at least one thermoplastic material such as a polycarbonate, a polyester, a polyvinylchloride, a polyurethane, a polyethylene, a polypropylene, polystyrene, a polyether, a polyamide, a polyimide, polytetrafluoroethylene or a copolymer thereof. In an embodiment, the at least one electrically insulating material may comprise or may be alumina. Suitable polyesters are, for example, selected from the group consisting of polyethylene terephthalate (PET), glycol modified polyethylene terephthalate, and polyethylene naphthalate. A suitable polyethylene is for example selected from the group consisting of high density polyethylene (HDPE) and low density polyethylene (LDPE).

Thus in a preferred embodiment the substrate comprises at least one electrically insulating material selected from the group consisting of an insulating epoxy resin, a polycarbonate, a polyester, a polyvinylchloride, a polyurethane, a polyethylene, a polypropylene, polystyrene, a polyether, a polyamide, a polyimide, polytetrafluoroethylene or a copolymer thereof, and alumina.

The substrate comprises a first side and a second side. To the person skilled in the art it is clear that the first side and the second side are different from one another.

In an embodiment the first side and the second side are positioned opposite each other. Therefore, in an embodiment the substrate comprises two opposing sides, the first side and the second side opposing the first side.

Thus it is preferred that in the analyte sensor according to the present invention, the first side and the second side of the substrate are positioned opposite each other.

The substrate may be a flat substrate or may be rod-shaped (i.e., round-shaped) if a wire-type sensor is utilized. Specifically the substrate may be flexible and/or deformable. In particular, the substrate may be bendable. Thus, as an example, the substrate may be a thin, flexible substrate. As an example, the substrate may have a thickness of 50 µm to 1 mm, specifically a thickness of 80 µm to 500 µm, such as 110 µm to 250 µm.

The substrate may have a length which is preferably less than 50 mm, such as a length of 30 mm or less, e.g. a length of 5 mm to 30 mm.

If the analyte sensor is an implantable sensor, preferably a partially implantable sensor, then the length of the substrate is measured in the insertion direction of the analyte sensor. The length of the substrate refers to the total length of the substrate. The "total length of the substrate" is the overall length of the substrate, including the insertable portion of the substrate which is within the body tissue of the user during use of the analyte sensor and the on body portion of the substrate. The "on body portion of the substrate" is the portion of the substrate which may, for example be connected to the electronics unit.

The analyte sensor comprises at least one working electrode positioned on the first side of the substrate. Preferably the at least one working electrode is positioned only on the first side of the substrate. This means, within the context of the present invention, that in an embodiment the second side does not comprise at least one working electrode.

The at least one working electrode is preferably adapted for detecting the analyte, in particular, the at least one working electrode is an electrode of the analyte sensor which is sensitive for the analyte.

The at least one working electrode comprises at least one electrically conductive material. "Electrically conductive material" within the context of the present invention refers to a material being capable of sustaining an electrical current. Thus, the at least one electrically conductive material may be selected from the group consisting of metals and nonmetallic electrically conductive materials.

Suitable metals are known as such and are, for example, selected from the group consisting of gold, nickel, platinum, and palladium, wherein gold is particularly preferred.

Suitable nonmetallic electrically conductive materials are for example selected from the group consisting of carbon, carbon paste, gold paste or conductive polymers. Suitable conductive polymers are, for example polyaniline and/or poly-3,4-ethylenedioxythiophene (PEDOT). Carbon paste may comprise, for example, carbon and at least one binder such as vinyl chloride co- and terpolymers. Carbon paste is known as such. Such a carbon paste is typically formed by combining the carbon and binder with a solvent such as diethylene glycol butyl ether and then removing the solvent in a drying step.

Thus, the at least one electrically conductive material of the at least one working electrode preferably is selected from the group consisting of gold, nickel, platinum, palladium, carbon, carbon paste, polyaniline and poly-3,4-ethylenedioxythiophene (PEDOT), particularly preferred, the at least one electrically conductive material of the at least one working electrode is selected from the group consisting of gold, carbon, and carbon paste. More preferably, the at least one electrically conductive material consists essentially of gold and/or carbon and/or carbon paste. Most preferably, the at least one electrically conductive material consists essentially of carbon and/or carbon paste. In an alternative embodiment, the at least one electrically conductive material has a layered structure wherein a first layer consists of gold and a second layer consists of carbon and/or carbon paste. In this particular embodiment, gold can be positioned on top of the first side of the substrate and on top of the gold, carbon and/or carbon paste can be positioned.

In particular, the at least one working electrode may comprise the at least one electrically conductive material in the form of at least one conductive trace. The term "conductive trace" within the context of the present invention refers, without limitations, to an electrically conductive strip, layer, wire or other type of electrical conductor. The conductive trace may have a thickness of at least 0.05 µm, preferably of at least 0.5 µm, more preferably of at least 5 µm, specifically of at least 7 µm, or at least 10 µm. In the case where the conductive trace comprises carbon or is carbon, the conductive trace may specifically have a thickness of at least 7 µm, more specifically of at least 10 µm. Specifically, in the case where the conductive trace is gold, the conductive trace may have a thickness of at least 50 nm, more specifically of at least 900 nm.

The at least one electrically conductive material may be positioned on the first side of the substrate by any known method, for example via chemical vapor deposition (CVD), physical vapor deposition (PVD), or a wet-coating process. Wet-coating processes are known as such. A suitable wet-coating process is for example selected from the group consisting of spin-coating, spray-coating, doctor-blading, printing, dispensing, slot-coating, dip coating and screen printing.

The at least one working electrode typically comprises at least one enzyme although it is also possible to employ an enzymeless working electrode. In sensors comprising a working electrode that comprises at least one enzyme, the at least one working electrode may comprise precisely one enzyme or a mixture of two or more enzymes. Precisely one enzyme is preferred. Specifically, the enzyme is capable of catalyzing a chemical reaction converting the analyte. Even more specifically the at least one enzyme is selected from the group consisting of a glucose oxidase (EC 1.1.3.4), a hexose oxidase (EC 1.1.3.5), an(S)-2 hydroxy acid oxidase (EC 1.1.3.15), a cholesterol oxidase (EC 1.1.3.6), a glucose dehydrogenase (EC 1.1.5.9), a galactose oxidase (EC 1.1.3.9), an alcohol oxidase (EC 1.1.3.13), an L-glutamate oxidase (EC 1.4.3.11), and an L-aspartate oxidase (EC 1.4.3.16). In particular, the at least one enzyme is a glucose oxidase (GOx) and/or modifications thereof. In a preferred embodiment, the at least one enzyme comprises a glucose dehydrogenase, particularly an FAD-dependent glucose dehydrogenase (FAD-GDH).

The at least one enzyme may be comprised in a sensing material. The sensing material which comprises the at least one enzyme may be located at least partially on the electrically conductive material of the at least one working electrode. In particular, the sensing material may cover at least a portion of the at least one conductive trace. The sensing material in conjunction with the conductive trace forms the at least one working electrode. In particular, the sensing material preferably forms a layer on the at least one electrically conductive material.

The sensing material may be applied by any known method to the at least one electrically conductive material, for example by a wet-coating process. A suitable wet-coating process is for example selected from the group consisting of spin-coating, spray-coating, doctor-blading, printing, dispensing, slot-coating, dip coating and screen printing. After the wet-coating process, the layer of the sensing material may be further treated. Such treatments are for example drying treatment, curing treatments and/or laser ablation treatments. Such treatments are known as such.

The term "sensing material", as used herein, is a broad term and is to be given its ordinary and customary meaning to a person of ordinary skill in the art and is not to be limited to a special or customized meaning. The term specifically may refer, without limitation, to a material that may be or may comprise at least a polymeric material; specifically it may be or may comprise at least a polymeric material and at least a metal containing complex. The metal containing complex may be selected from the group of transition metal element complexes, specifically the metal containing complex may be selected from osmium-complexes, ruthenium-complexes, vanadium-complexes, cobalt-complexes, and iron-complexes, such as ferrocenes, such as 2-aminoethyl-ferrocene. Even more specifically, the sensing material may be a polymeric transition metal complex as described for example in WO 01/36660 A2, the content of which is included by reference. In particular, the sensing material may comprise a modified poly(vinylpyridine) backbone loaded with poly(bi-imidizyl) Os complexes covalently coupled through a bidentate linkage. A suitable sensing material is further described in Feldmann et al, Diabetes Technology & Therapeutics, 5 (5), 2003, 769-779, the content of which is included by reference. Suitable sensing materials further may include ferrocene-containing poly-acrylamide-based viologen-modified redox polymer, pyrrole-2,2'-azino-bis(3-ethylbenzthiazoline-6-sulfonic acid) (ABTS)-pyrene, Naphthoquinone-LPEI. The polymeric transition metal complex may represent a redox mediator incorporated into a cross-linked redox polymer network. This is advantageous as it may facilitate electron transfer between the at least one enzyme or analyte and the conductive trace. In order to avoid a sensor drift, the redox mediator and the enzyme may be covalently incorporated into a polymeric structure.

In an embodiment the sensing material may comprise a polymeric material and $MnO_2$-particles or any other material catalyzing hydrogen peroxide oxidation reaction as well as the at least one enzyme. Another material catalyzing hydrogen peroxide oxidation reaction is Pt (platinum).

Moreover, the sensing material may additionally comprise at least one crosslinker; the crosslinker may for example be capable of crosslinking at least part of the sensing material. Specifically the sensing material may comprise at least one crosslinker selected from UV-curable crosslinkers and chemical crosslinkers; more specifically the sensing material comprises a chemical crosslinker. Alternatively, the sensing material may be free of any crosslinker. "Free of any crosslinker" as used herein, is a broad term and is to be given its ordinary and customary meaning to a person of ordinary skill in the art and is not to be limited to a special or customized meaning. The term specifically may refer to a concentration of crosslinker in the range from 0 to 0.5 wt-% based on the dry weight of the sensing material. The term "dry weight" as used herein refers to the dry matter of the respective material, e.g. the material without the addition of any water or other solvent.

Suitable chemical crosslinkers according to the present invention are preferably selected from the group consisting of epoxide based crosslinkers, such as diglycidyl ethers like poly(ethylene glycol) diglycidyl ether (PEG-DGE) and poly (propylene glycol) diglycidyl ether; trifunctional short chain epoxides; anhydrides; diglycidyl ethers such as Resorcinol diglycidyl ether, Bisphenol A diglycidyl ether, Diglycidyl 1,2-cyclohexanedicarboxylate, Poly(ethylene glycol) diglycidyl ether, Glycerol diglycidyl ether, 1,4-Butanediol diglycidyl ether, Poly(propylene glycol) diglycidyl ether, Bisphenol diglycidyl ether, Poly(dimethylsiloxane), diglycidyl ether, Neopentyl glycol diglycidyl ether, 1,2,7,8-Diepoxyoctane, 1,3-Glycidoxypropyl-1,1,3,3-Tetramethyldisioxane; triglycidyl ethers such as N,N-Diglycidyl-4-glycidyloxyaniline, Trimethylolpropane triglycidyl ether; and tetraglycidyl ethers such as Tetrakisepoxy cyclosiloxane, Pentaerythritol tetraglycidyl ether, tetraglycidyl-4,4'-methylenebisbenzenamine.

The term "chemical crosslinker" as used herein, is a broad term and is to be given its ordinary and customary meaning to a person of ordinary skill in the art and is not to be limited to a special or customized meaning. The term specifically may refer, without limitation, to a crosslinker that is capable of initiating a chemical reaction generating a crosslinked molecular network and/or a cross-linked polymer when exposed to heat. "Exposed to heat" may refer to being exposed to a temperature above 15° C., specifically to a temperature above 20° C.; more specifically to a temperature in the range from 20° C. to 50° C. and even more specifically to a temperature in the range from 20° C. to 25° C. More specifically, chemical crosslinkers may initiate crosslinking of the sensing material when exposed to heat.

The term "UV-curable crosslinker" as used herein, is a broad term and is to be given its ordinary and customary meaning to a person of ordinary skill in the art and is not to be limited to a special or customized meaning. The term specifically may refer, without limitation, to the ability of a chemical substance of initiating a photochemical reaction generating a crosslinked molecular network and/or a cross-linked polymer when irradiated by light in the UV spectral range. More specifically, UV-curable crosslinkers may initiate crosslinking of the layer of the sensing material when irradiated by UV light.

Suitable UV curable crosslinkers according to the present invention include: benzophenone, diazirine and azide. Particularly suitable UV-curable crosslinkers are for example selected from the group consisting of, benzophenone comprising cross-linkers, poly(Di(2-hydroxy 3 aminobenzophenonepropylene) glycol), Dibenzophenone 1,2-cyclo-hexanedicarboxylate, Bis [2-(4-azidosalicylamido)ethyl] Disulfide, reaction products of the reaction of 4-aminoben-zophenone with any one of the above for the chemical cross-linker described di-glycidyl cross-linkers, triglycidyl cross-linkers and tetraglycidyl cross-linkers, an example of such a reaction product is 2,4,6,8-Tetramethyl-2,4,6,8-tetra-kis(2-hydroxy 3-aminpropylbenzophenone)-cyclotetrasi-loxan, and reaction products of the reaction of 4-Benzoyl-benzoic Acid N-Succinimidyl Ester with a diamin or a jeffamin.

The analyte sensor furthermore comprises at least one second electrode positioned on the second side of the substrate. Preferably, the at least one second electrode is positioned only on the second side of the substrate. This means, within the context of the present invention, that in an embodiment, the first side does not comprise at least one second electrode. In an embodiment, precisely one second electrode is positioned on the second side of the substrate. Preferably, the at least one second electrode does not com-prise an enzyme. Thus, preferably, the at least one second electrode is free of the at least one enzyme. Preferably, the second side of the substrate is free of enzyme.

The at least one second electrode may be selected from the group consisting of a counter electrode, a reference electrode, and a combined counter/reference electrode. Pref-erably, the at least one second electrode is a combined counter/reference electrode.

The at least one second electrode comprises silver. "Sil-ver" within the context of the present invention does not only encompass elemental silver, but also any silver con-taining compound. Therefore, the at least one second elec-trode comprises elemental silver and/or at least one silver containing compound. A preferred silver containing com-pound is silver chloride (AgCl). For example, the at least one second electrode comprises elemental silver and/or silver chloride. In particular, the at least one second electrode can comprise elemental silver and silver chloride. In particular, the at least one second electrode can comprise silver/silver chloride (Ag/AgCl). Preferably, the silver which the second electrode comprises corresponds to the silver of the first and second silver layers, which are described in further detail below.

Thus, an analyte sensor which comprises at least one second electrode which comprises Ag/AgCl is preferred.

For example, the load of AgCl of the at least one second electrode is typically in the range from 20 μg to 150 μg. If two or more second electrodes are comprised, then the load of AgCl of the at least one second electrode refers to the sum of the load of AgCl of the two or more second electrodes. The load of AgCl of the at least one second electrode refers to the load when the analyte sensor is manufactured and refers to the sum of the loads of the first and second silver layers. The first and second silver layers are formed from first and second silver compositions applied as first and second silver composition regions in pre-cut sensors, wherein the first and second silver compositions and first and second silver composition regions each comprise silver. It is clear to the skilled person that the load may change during use of the analyte sensor, for example due to the formation of elemental Ag from AgCl.

The minimum load of AgCl of the at least one second electrode may be calculated according to the following formula.

$$m(\text{AgCl}) = \frac{M(\text{AgCl}) * I * t}{z * F}$$

wherein

I is the average current in A while the analyte sensor is in use t is the total wear time of the sensor in s F is the Faraday constant in C/mol Z is the charge number of silver (z=1)

M(AgCl) is the molar mass of AgCl m(AgCl) is the load of AgCl of the at least one second electrode.

Ag/AgCl which the at least one second electrode in an embodiment comprises may be comprised in a binder. Suitable binders are known as such and are, for example, selected from the group consisting of metallic binders, ceramic binders and polymeric binders. Preferred are poly-meric binders, in particular physically binding polymer binders and/or chemically binding polymer binders.

The at least one second electrode comprises at least one first silver layer and at least one second silver layer, wherein the second silver layer partially overlaps with the first silver layer. The first and the second silver layers partially overlap with one another to provide for mass transport therebetween. The first silver layer and the second silver layer partially overlap with one another, but do not completely overlap with each other. In other words, the first silver layer and the second silver layer are not coextensive. The first silver layer and the second silver layer can comprise the same compo-sition. With respect to the term "the same composition", this means that the components comprised in the first silver layer and in the second silver layer are identical. Their amounts do not have to be identical however. Preferably, the components and their respective amounts comprised in the first and the second silver layers are identical. Preferably, the sensor comprises exactly one first silver layer and exactly one second silver layer.

While not wishing to be bound by theory, the sensors as described herein provide a "storage vessel" concept where the overall quantity of the AgCl is not directly linked to the exposed AgCl area and vice versa. Further, the exposed portion of the AgCl in sensors described herein is kept below a certain threshold, but, simultaneously, the overall AgCl quantity is sufficient for the proper sensor operation when placed in a user's body for a desired period of use, e.g., 14 days as one example. In general, it is desired to have as much AgCl in the composition as possible, as this is the material which is being used up during sensor operation.

In an example, the second silver layer of the at least one second electrode serves as the "storage vessel" of AgCl and may comprise AgCl/Ag in a weight/weight ratio of 9:1 or even higher. The binder quantity is as little as possible, but as much as needed, since the binder has no chemical function, but only holds Ag and AgCl particles together. The first silver layer of the at least one second electrode provides the at least one exposed area of the first silver layer in finished sensors as described above. In the first silver layer, the weight/weight ratio of AgCl/Ag is typically inversely proportional to the amount of the exposed area since AgCl presents biocompatibility issues in the host's body. In an embodiment, the first silver layer may comprise a weight/weight ratio of 9:1 AgCl/Ag, if the exposed area does not exceed 0.01 mm².

The AgCl content of the first silver layer depends on its cut cross-section and type of binder. The AgCl content in the first silver layer preferably is well below 30 wt. % based on the total weight of the first silver layer. The AgCl content of the second silver layer may vary in a wider range as is clear from the description above and can comprise an amount up to 99 wt. % AgCl (no Ag) based on the total weight of the second silver layer.

The thicknesses, widths and lengths, as well as the AgCl content of each silver layer depend on the overall demand for AgCl, maximum allowable exposed AgCl area, binder type in the pastes and other parameters.

In an aspect of the invention, the dry thicknesses of the coatings of the first and second silver layers typically range from 1 to 100 μm. The preferred values for layer thicknesses can depend on the selected manufacturing process, e.g., slot-die coating, screen printing or rotary screen printing, and are generally about 15 μm for each layer.

In the sensors as described herein (i.e., finished sensors), the term "length" should be understood as referring to a dimension extending longitudinally of the sensor whereas the term "width" should be understood as referring to a dimension extending transversely of the sensor. The length of the first silver layer typically lies in a wide range from a sub-millimeter scale to several millimeters, depending on the design of the sensor. The preferred length of the first silver layer lies in the range of 1-6 mm, most preferably about 4 mm.

The width of the second silver layer is limited by the sensor width and may not exceed it. For a sensor having a 700 μm width, the second silver layer preferably has a width of 300 to 500 μm. In certain embodiments, the length of the second silver layer is less than the first layer length and preferably lies in the range of 1-6 mm, more preferably about 4 mm. To be clear, the length of the second silver layer may also exceed or as noted above, be less than the length of the first silver layer.

The analyte sensor further comprises at least one exposed area of the first silver layer, wherein the at least one exposed area is disposed on the exterior of the sensor and configured to be in direct contact with body fluid when the sensor is implanted in a user. Preferably, the sensor comprises a plurality of the exposed areas, and more preferably comprises at least one such exposed area on each lateral side of the sensor. Preferably, the second silver layer is not exposed (i.e., is disposed only on the interior of the sensor and is not disposed on the exterior of the sensor and is not configured to be in direct contact with body fluid when the sensor is implanted in a user) and only has indirect contact to the body fluid via the first silver layer in implanted sensors. In other words, the second silver layer is disposed only on the interior of the sensor and is not disposed on the exterior of the sensor and is not configured to be in direct contact with body fluid when the sensor is implanted in a user. Further, the second silver layer can be the upper or the lower layer (and hence, the first silver layer can be the lower or the upper layer) in analyte sensors of the invention. In other words, in manufacturing of the finished sensors, it is envisioned that the second silver layer could be applied first and the first silver layer could be applied next It is envisioned that a semi-simultaneous application of the first and second silver layers could be provided during manufacturing, i.e., wherein for example two separate tools are provided for layer application, but they are installed one after another in the manufacturing line and apply the corresponding layers nearly simultaneously in time, but one after another relative to the treated substrate. For instance, two screen printing or diecoating machines could be utilized and installed next to each other in the manufacturing line, and the substrate could go through each machine.

The second silver layer intersects with the first silver layer and partially overlaps with the first silver layer to form an overlapping region.

In an embodiment, the first silver layer intersects with the second silver layer to form a + shape design. Here, it should be understood that the + shape design refers to a configuration of the at least one second electrode wherein the first and second silver layers intersect and partially overlap to form a + shape. It should be understood that the + shape also encompasses a cross-shaped design where the first and the second silver layers intersect and partially overlap but do not bisect one another.

In an embodiment, the first silver layer intersects with the second silver layer to form a T shape design. Here, it should be understood that the T shape design refers to a configuration of the at least one second electrode wherein the first and second silver layers intersect and partially overlap to form a T shape. It should be understood that the T shape also encompasses a design where the first and the second silver layers intersect and partially overlap but wherein the length of the second silver layer does not extend to the full length of the first silver layer or vice versa.

In an embodiment, the first silver layer intersects with the second silver layer to form an X shape design. Here, it should be understood that the X shape design refers to a configuration of the at least one second electrode wherein the first and second silver layers intersect and partially overlap to form an X shape. It should be understood that the X shape design is constructed in the same way as described above with respect to the T shape design, but wherein the first and second silver layers form an acute angle with respect to each other (i.e., the first and second silver layers are not perpendicular with respect to each other). It should be understood that this X shape design also encompasses a design wherein the length of the second silver layer does not extend to the full length of the first silver layer or vice versa.

The at least one second electrode may comprise at least one second conductive trace. The at least one second conductive trace is preferably positioned on the second side of the substrate. In particular, the first side of the substrate preferably does not comprise a second conductive trace.

The term "second conductive trace" specifically may refer, without limitation, to an electrically conductive strip, layer, wire or other type of elongated electrical conductor. In particular, the term may refer to at least one second electrically conductive material. Hence, the at least one second conductive trace is preferably capable of sustaining an electrical current. For example, the at least one second electrically conductive material may be selected from the group consisting of gold, nickel, platinum, palladium, carbon, carbon paste, polyaniline and poly-3,4-ethylenedioxythiophene (PEDOT). Particularly preferred, the at least one second electrically conductive material of the at least one second electrode is selected from the group consisting of gold, carbon, and carbon paste. More preferably, the at least one second electrically conductive material consists essentially of gold and/or carbon and/or carbon paste. In an alternative embodiment, the at least one second electrically conductive material has a layered structure wherein a first layer consists of gold and a second layer consists of carbon and/or carbon paste. In this alternative embodiment, gold can be positioned on top of the second side of the substrate and on top of the gold, carbon and/or carbon paste can be positioned.

It is preferred that silver which the at least one second electrode comprises is positioned on top of the at least one second conductive trace. Thus, it is preferred, that Ag/AgCl is positioned at least partially on top of the at least one second conductive trace, in particular on top of the layered structure of the at least one second electrically conductive material. Further, typically, the first layer of the at least one second electrode is positioned at least partially on top of the at least one second conductive trace. Silver, preferably Ag/AgCl, and the at least one second conductive trace, in particular the layered structure of the at least one second conductive material, form the at least one second electrode.

The at least one second conductive trace and the at least one second electrically conductive material may be applied to the second side of the substrate by the same methods as the methods by which the at least one conductive trace and the at least one electrically conductive material of the at least one working electrode are applied to the first side of the substrate. Thus, the embodiments and preferences described above hold true. The methods for applying the at least one second conductive trace and the at least one second electrically conductive material of the second electrode and the methods for applying the at least one conductive trace and the at least one electrically conductive material of the working electrode may be selected independent from one another.

Silver, in particular Ag/AgCl, comprised in the at least one second electrode may be applied to the second side of the substrate, in particular at least partially on top of the at least one second conductive trace, by the same methods as the methods by which the sensing material of the at least one working electrode is applied to the first side of the substrate. Thus, the embodiments and preferences described above hold true. The method for applying silver, in particular Ag/AgCl, comprised in the at least one second electrode and the method for applying the sensing material comprised preferably in the at least one working electrode may be selected independent from one another.

The analyte sensor of the present invention comprises a membrane. The membrane comprises a polymer composition which comprises a hydrophobic polymer and is located on top of the at least one second electrode.

In an embodiment, the term "membrane" within the context of the present invention refers to a layer of at least one material which provides a barrier. In an embodiment, which is particularly preferred, the term "membrane" within the context of the present invention refers to a layer of at least one material which is essentially impermeable. "Essentially impermeable" means that the membrane has a water uptake of less than 1% by weight, based on the total weight of the membrane.

For example, the membrane may have a thickness in the range from 1 μm to 100 μm, preferably in the range from 5 μm to 15 μm.

The membrane is located on top of the at least one second electrode.

"Located on top of the at least one second electrode" means that the membrane covers the at least one second electrode.

As mentioned above, the sensor comprises at least one exposed area of the first silver layer disposed on the exterior of the sensor, and preferably a plurality of such exposed areas, most preferably two. The exposed area(s) can also be referred to as open area(s) since they form at least a portion of an exterior exposed surface of the sensor.

In a preferred embodiment of the present invention, the at least one working electrode does not comprise the membrane comprising the polymer composition which comprises the hydrophobic polymer.

Thus, an analyte sensor is preferred in which the at least one working electrode is free of the membrane comprising the polymer composition which comprises the hydrophobic polymer.

The membrane comprises a polymer composition which comprises a hydrophobic polymer.

"Hydrophobic" within the context of the present invention means that the polymer has a water uptake in the range from 0 to 5% by weight, in an embodiment a water uptake of less than 1% by weight, based on the total weight of the polymer.

Thus, an analyte sensor is preferred, wherein the hydrophobic polymer has a water uptake of less than 1% by weight, based on the total weight of the hydrophobic polymer.

The hydrophobic polymer is preferably a thermoplastic hydrophobic polymer.

The hydrophobic polymer, for example, has a glass transition temperature in the range from −100° C. to 0° C., preferably in the range from −70° C. to −50° C. The glass transition temperature may be measured via differential scanning calorimetry using a ramp of 10° C./min for heating and cooling. The glass transition temperature is measured during the second heating cycle. This means that first, the hydrophobic polymer is heated with a ramp of 10° C./min, then it is cooled with a ramp of 10° C./min and then it is heated again with a ramp of 10° C./min to determine the glass transition temperature.

The hydrophobic polymer, for example, has a crystallization temperature in the range from 50° C. to 100° C., for example in the range from 75° C. to 85° C. The crystallization temperature is measured via differential scanning calorimetry using the same parameters as for the glass transition temperature.

Thus, an analyte sensor is preferred wherein the hydrophobic polymer has a glass transition temperature, wherein the glass transition temperature is in the range from −100° C. to 0° C.

This glass transition temperature is particularly advantageous as it results in a sufficiently high stability of the membrane. If the sensor is bent, in particular during use, the membrane will not or only to a small extent be damaged.

The hydrophobic polymer may be any hydrophobic polymer known to the skilled person. Preferably, the hydrophobic polymer is selected from the group consisting of thermoplastic polyurethanes (TPU), thermoplastic polyurea, polyethylene, polypropylene, polystyrene, butyl methacrylate polymers (BUMA), polyethylene terephtalate (PET), and UV hardening resins, such as acrylated silicones, acrylated urethanes, acrylated polyesters and/or acrylated epoxides. Preferably, the hydrophobic polymer is a thermoplastic polyurethane.

Therefore, an analyte sensor is preferred, wherein the polymer composition comprises a hydrophobic thermoplastic polyurethane.

The hydrophobic thermoplastic polyurethane may comprise hard segments and soft segments in various ratios. Suitable hard segments usually comprise a polymerization product of a diisocyanate and a polyol. A suitable diisocyanate may be an aliphatic diisocyanate or an aromatic diisocyanate, preferably an aliphatic diisocyanate.

Suitable aromatic diisocyanates are for example, 4,4'-methylene diphenyl diisocyanate, and/or toluene-2,4-diisocyanate.

Suitable aliphatic diisocyanates are for example, hexamethylene diisocyanate, and/or isophorone diisocyanate.

A suitable polyol is preferably a diol, such as 1,4-butanediol, 1,5-pentanediol, 1,6-hexanediol, and/or 1,10-decanediol.

Suitable soft segments may comprise polyethers and/or polyesters. Suitable polyethers are for example polyethylene oxide and/or polytetrahydrofurane, whereas suitable polyesters are for example polyethylene terephthalate and/or polyethylene naphthalate.

The polymer composition may comprise further components.

The analyte sensor may comprise at least one third electrode. Preferably, the analyte sensor does not comprise at least one third electrode.

If at least one third electrode is comprised in the analyte sensor, then the at least one second electrode is preferably selected from the group consisting of a counter electrode and a reference electrode. The at least one third electrode is then preferably also selected from the group consisting of a counter electrode and a reference electrode. If the at least one second electrode is a counter electrode, then the at least one third electrode is a reference electrode and vice versa.

The analyte sensor may further comprise at least one flux limiting membrane.

The at least one flux limiting membrane is specifically at least positioned on top of the at least one working electrode. The at least one flux limiting membrane can also be positioned on top of the membrane comprising the polymer composition which comprises the hydrophobic polymer.

The term "flux limiting membrane", as used herein, is a broad term and is to be given its ordinary and customary meaning to a person of ordinary skill in the art and is not to be limited to a special or customized meaning. The term specifically may refer, without limitation, to a layer of at least one material, which provides a selective barrier. Thus, the flux limiting membrane generally may selectively allow for one or more molecules and/or compounds to pass, whereas other molecules and/or compounds are stopped by the flux limiting membrane. Thus, the flux limiting membrane is permeable for the at least one analyte to be detected. Thus, as an example, the flux limiting membrane may be permeable for one or more of glucose, lactate, cholesterol or other types of analytes. The at least one flux limiting membrane may, hence, function as a diffusion barrier that controls diffusion of the analyte from the exterior, e.g. the body fluid surrounding the analyte sensor, to the sensing material, i.e., typically to the at least one enzyme which the at least one working electrode may comprise. In addition, the at least one flux limiting membrane may function as a biocompatibility membrane layer as mentioned elsewhere herein.

The at least one flux limiting membrane, as an example, may have a thickness sufficient for providing mechanical stability. The at least one flux limiting membrane specifically may have a thickness of 1 μm to 150 μm. For the at least one flux limiting membrane, as outlined herein, several materials may be used, standalone or in combination. Thus, as an example, the flux limiting membrane specifically may comprise at least one polymeric material. Suitable polymeric materials may, for example be selected from the group consisting of a polyvinylpyridine based copolymer, a polyurethane and a hydrogel. Polyvinylpyridine based copolymers are particularly suitable.

Suitable hydrogels are in particular polyethylene glycol copolymers (PEG copolymers), polyvinyl acetate copolymers (PVA copolymers), poly(2-alkyl-2-oxazonline) copolymers, polyacrylate and/or methacrylate-acrylate copolymers or block-copolymers, in particular polyacrylate and/or methacrylate-acrylate copolymers or block-copolymers comprising hydrophilic side groups. Thus, as an example, suitable hydrogels may be selected from the group consisting of (hydroxyethyl) methacrylate (HEMA)-homopolymers, HEMA-copolymers, silicon hydrogels and HEMA-co-N-vinylpyrrolidone-polymers, each of which may comprise side groups selected from the group consisting of methacrylic acid, glycerol methacrylate, N,N-dimethylacrylamide and phospharylcholine.

These types of flux limiting membranes are generally known in the art. As an example, flux limiting membranes as disclosed in e.g. EP2697388 A1, WO 2007/071562 A1 and/or in WO 2005/078424 A1 may be used. Specifically, the polymeric material may have a weight average molecular weight (MW) of more than 10.000 kDa. More specifically, the polymeric material may have a weight average molecular weight (MW) of more than 50.000 kDa, or even more than 100.000 kDa. Particularly suitable are polymeric materials with a weight average molecular weight (MW) of 10.000 to 500.000 kDa. The polymeric material of the flux limiting membrane may be the same as or may be different from the polymeric material of the sensing material.

The analyte sensor may further comprise at least one biocompatibility membrane.

The at least one biocompatibility membrane is specifically at least positioned on top of the at least one working electrode. Preferably, the at least one biocompatibility membrane is also positioned on top of the membrane comprising the polymer composition which comprises the hydrophobic polymer. In particular, the at least one biocompatibility membrane is positioned on top of the flux limiting membrane which is in an embodiment of the present invention comprised in the analyte sensor. Specifically, the biocompatibility membrane fully covers the at least one flux limiting membrane. The term "fully covers" within the context of the present invention means that, specifically, the flux limiting membrane is not in direct contact with a body fluid if the analyte sensor is in use, but only the biocompatibility membrane is in direct contact with the body fluid. This means that at least the implantable portion of the analyte sensor is preferably fully covered by the at least one biocompatibility membrane.

The term "biocompatibility membrane", also denoted biocompatibility layer, as used herein, relates to a layer, in particular an outmost layer of the analyte sensor or part thereof, consisting of a biocompatible material. Specifically, the biocompatibility layer has a thickness of from 1 μm to 10 μm, in an embodiment of from 3 μm to 6 μm. More specifically, the biocompatibility layer covers the analyte sensor at least partly or completely. Even more specifically, the biocompatibility layer may be the outmost layer of the analyte sensor. Thus, even more specifically, at least a part of the biocompatibility layer contacts a body fluid of a subject. For example, the biocompatibility layer may be not diffusion-limiting for the analyte as specified elsewhere herein. For example, the biocompatibility layer may be not diffusion-limiting for small molecules having a molecular weight of less than 2.000 Da, in an embodiment less than 1.000 Da. For example, the biocompatibility layer may not comprise an added enzyme. For example, the biocompatibility layer may not comprise an added polypeptide. As will be understood by the skilled person, this does not exclude that enzyme or polypeptide molecules diffuse into the biocompatibility layer from adjacent layers, tissues, or body fluids.

The term "biocompatible material", as used herein relates to a material suitable for use with living tissue or a living system by not being or being to a reduced extent toxic, injurious, or physiologically reactive and/or causing to a reduced extent or not causing immunological rejection. In an embodiment, the biocompatible material is a material not inducing a bodily response, e.g. an inert material or a material comprising chemical compounds preventing bodily responses from occurring in the vicinity of the biocompatibility layer. In another embodiment, the biocompatible material is a material pre-venting cells from attaching to said biocompatibility layer. The biocompatibility membrane may be or may comprise at least one material selected from the group consisting of methacrylate based polymers and copolymers, such as acrylamide-methacrylate based copolymers, biodegradable polysaccharides such as hyaluronic acid (HA), agarose, dextran and chitosan. Further biocompatible materials are disclosed in WO 2019/166394 A1 and include nonbiodegradable synthetic hydrogels such as hydrogels prepared from the copolymerization of 2-hydroxyethyl methacrylate (HEMA), 2-hydroxypropyl methacrylate (HPMA), acrylamide (AAm), acrylic acid (AAc), N-isopropylacrylamide (NIPAm), and methoxyl poly(ethylene glycol) (PEG) monoacrylate (mPEGMA or PEGMA), with cross-linkers, such as N,N'-methylenebis(acrylamide) (MBA), ethylene glycol diacrylate (EGDA) and PEG diacrylate (PEGDA), Pluronic® polymers with a structure of poly(ethylene oxide) (PEO)-poly(propylene oxide) (PPO)-PEO, chemical cross-linking of modified poly(vinyl alcohol) (PVA), Poly(4vinylpyridine), PEG.

Another aspect of the present invention is a method for manufacturing an analyte sensor, in particular the inventive analyte sensor, the method comprising the steps:

a) providing a raw substrate which comprises a first side and a second side, b) preparing a working electrode region on the first side of the raw substrate, the preparing of the working electrode region comprising the steps:

b1) applying an electrically conductive material to the first side of the raw substrate, b2) applying a sensing material at least partially on the electrically conductive material, c) preparing a second electrode region on the second side of the raw substrate, the preparing of the second electrode region comprising the steps:

c1) applying a first silver composition to form a first silver composition region on the second side of the raw substrate, c2) applying a second silver composition as a plurality of separated second silver composition regions on the second side of the raw substrate, wherein the second silver composition has the same composition as the first silver composition and wherein the second silver composition is applied over the first silver composition such that the second silver composition regions partially overlap with the first silver composition region or the first silver composition is applied over the second silver composition so that the first silver composition region partially overlaps with the second silver composition regions, d) applying a polymer composition on top of the second electrode region, to obtain a membrane, wherein the polymer composition comprises a hydrophobic polymer, and e) cutting the raw substrate, the working electrode region, the second electrode region and the membrane, wherein only the first silver composition region of the second electrode region is cut, to obtain the analyte sensor.

Process steps a) to e) may be carried out in the given order. However, it is also possible to carry out the steps in different orders. In particular, the order of steps b) and c) may be different. It is even possible, to first carry out step b1), then step c1) and thereafter step b2), for example. Further process steps are feasible. It is also possible to carry out at least one of process steps a) to e) more than once. For example, step c1) may be carried our more than once, so that more than one layer of the silver composition is obtained. Furthermore, step c2) can be carried out in successive steps, simultaneous steps, or a combination thereof, wherein a plurality of second silver composition regions are applied. Lastly, although step c1) can be carried out prior to step c2), in another embodiment, step c2) can be carried out before step c1).

In step a) of the method for manufacturing the inventive analyte sensor, a raw substrate is provided.

Within the context of the present invention, the term "raw substrate" specifically may refer, without limitation, to any kind of material or combination of materials which is suitable to form a carrier layer to support the at least one working electrode and the at least one second electrode. From the raw substrate, the substrate of the inventive analyte sensor may be manufactured, for example, by cutting the raw substrate. In particular, the raw substrate may comprise an electrically insulating material. For the electrically insulating material, the embodiments and preferences described above for the electrically insulating material of the substrate hold true.

Thus, in a preferred embodiment the raw substrate comprises at least one electrically insulating material selected from the group consisting of an insulating epoxy resin, a polycarbonate, a polyester, a polyvinylchloride, a polyurethane, a polyether, a polyethylene, a polyamide, a polyimide, a polyacrylate, a polymethacrylate, a polytetrafluoroethylene or a copolymer thereof, and alumina.

A suitable polyester is for example polyethylene terephthalate.

The raw substrate comprises a first side and a second side. To the person skilled in the art it is clear that the first side and the second side are different from one another.

In an embodiment the first side and the second side are positioned opposite each other. Therefore, in an embodiment the raw substrate comprises two opposing sides, the first side and the second side opposing the first side.

The raw substrate may be a flat substrate or may be rod-shaped (e.g., round-shaped) if a needle-type sensor is desired. Specifically the raw substrate may be flexible and/or deformable. Thus, as an example, the raw substrate may be a thin, flexible raw substrate. As an example, the raw substrate may have a thickness of 50 µm to 1 mm, specifically a thickness of 80 µm to 500 µm, such as 110 µm to 250 µm.

The raw substrate may have a length which is preferably in the range from a few centimeters to several meters, such as for example in the range from 10 cm to 100 m.

The raw substrate may have a width which is preferably in the range from 2 centimeters (cm) to 8 cm.

In an embodiment, the raw substrate may comprise an electrically conductive material on at least one of the first and the second side, preferably on the first side and on the second side.

In an embodiment of the present invention, the raw substrate may be suitable to be used in a roll-to-roll process.

The raw substrate may be provided by any method known to the skilled person. For example, the raw substrate may be provided as a roll. This is particularly advantageous as the raw substrate may then be used in a roll-to-roll process.

In an embodiment, the raw substrate is cut into sheets before the working electrode region is prepared. The sheets may have any length, such as, for example, in the range from 100 mm to 300 mm.

In step b) a working electrode region is prepared on the first side of the raw substrate.

The working electrode region specifically comprises all components which form part of the at least one working electrode of the analyte sensor.

In step b1) the electrically conductive material is applied to the first side of the raw substrate. For the electrically conductive material the embodiments and preferences described above hold true.

The electrically conductive material can be applied to the first side of the raw substrate by any known method, for example via chemical vapor deposition (CVD), physical vapor deposition (PVD), or a wet-coating process. Wet-coating processes are known as such. A suitable wet-coating process is for example selected from the group consisting of spin-coating, spray-coating, doctor-blading, printing, dispensing, slot-coating, dip coating and screen printing.

In step b2) a sensing material which may typically comprise at least one enzyme is applied at least partially on the electrically conductive material. For the sensing material and the at least one enzyme, the embodiments and preferences described above hold true.

The sensing material may be applied by any known method to the at least one electrically conductive material, for example by a wet-coating process. A suitable wet-coating process is for example selected from the group consisting of spin-coating, spray-coating, doctor-blading, printing, dispensing, slot-coating, dip coating and screen printing. After the wet-coating process, the layer of the sensing material may be further treated. Such treatments are for example drying treatments, curing treatments and/or laser ablation treatments. Such treatments are known as such.

The sensing material may be applied to the electrically conductive material so that it fully or partially covers the electrically conductive material, and it may also overlap with the electrically conductive material. The sensing material may be applied to the electrically conductive material in any shape, for example, in the shape of one or a plurality of lines, one or a plurality of dots, or one or a plurality of strips. It is also possible to remove the sensing material partially from the at least one electrically conductive material after its application. Methods to remove the sensing material partially from the at least one electrically conductive material are known as such. For example, a portion of the sensing material may be irradiated by light, in particular by a laser, thereby removing the sensing material partially. It is also possible to irradiate a portion of the sensing material, thereby crosslinking the sensing material and afterwards washing the non-irradiated portion away.

In step c) a second electrode region is prepared on the second side of the raw substrate.

The second electrode region specifically comprises all components which form part of the at least one second electrode of the analyte sensor.

In step c1) a first silver composition is applied to form a first silver composition region which is essentially continuous on the second side of the raw substrate. In an embodiment, the first silver composition is applied directly to the second side of the raw substrate. The first silver composition may be applied to the second side of the raw substrate so that it covers the second side of the raw substrate at least partially. In one embodiment, the first silver composition is applied as a continuous strip extending along the length of the raw substrate to form the first silver composition region. In another embodiment, the silver composition is applied at least partially to a second conductive trace.

The silver composition may be any composition known to the skilled person. In particular, the silver composition comprises silver. "Silver" within the context of the silver composition of the present invention not only encompasses elemental silver but also silver compounds. In particular, the silver composition comprises Ag/AgCl and a polymer binder. For the polymer binder and for Ag/AgCl the preferences and embodiments described above hold true.

In an embodiment, before step c1) a second conductive trace is applied to the raw substrate. For the second conductive trace the embodiments and preferences described above hold true. Thus, the second conductive trace may refer to a second electrically conductive material. For the second conductive material, the embodiments and preferences described above hold true.

The second electrically conductive material can be applied to the first side of the raw substrate by any known method, for example via chemical vapor deposition (CVD), physical vapor deposition (PVD), or a wet-coating process. Wet-coating processes are known as such. A suitable wet-coating process is for example selected from the group consisting of spin-coating, spray-coating, doctor-blading, printing, dispensing, slot-coating, dip coating and screen printing.

In step c2) the second silver composition is applied as a plurality of separated second silver composition regions on the second side of the raw substrate, wherein the second silver composition has the same composition as the first silver composition and wherein the second silver composition is applied over the first silver composition such that the second silver composition regions partially overlap with the first silver composition region or the first silver composition is applied over the second silver composition so that the first silver composition region partially overlaps with the second silver composition regions. The plurality of separated regions ultimately form the second silver layers of finished analyte sensors.

Note that in accordance with the language above relating to an embodiment were step c2) is carried out prior to step c1), if step c2) is carried out first, then the second silver composition would be applied as a plurality of separated second silver composition regions on the second side of the raw substrate, and next the first silver composition would be applied in step c1) so that the first and second silver composition regions partially overlap.

As further used herein, the term "coating process" may refer to an arbitrary process for applying at least one layer to at least one surface of an arbitrary object. The applied layer may cover the object, for example another layer of silver composition material and/or the sensor substrate completely or may only cover a part or parts of the object. The layer may be applied via a coating process wherein a material is provided, e.g. in a liquid form, exemplarily as a suspension or as a solution, and may be distributed on the surface.

The silver composition may be applied to the second side of the raw substrate by any known method, for example by a wet-coating process. A suitable wet-coating process is for example selected from the group consisting of spin-coating, spray-coating, doctor-blading, printing, dispensing, slot-coating, dip coating, screen printing, and cannula-coating. After the coating process, the layer of the silver composition may be further treated. Such treatments are for example drying treatments, curing treatments and/or laser ablation treatments. Such treatments are known as such.

In particular embodiments, the step for applying the silver composition is carried out via cannula-coating. In certain embodiments, the cannula used in the coating process may be a metal cannula or a polymer cannula, e.g. PTFE cannula or a steel cannula. In certain embodiments, the cannula has an inner diameter of about 0.15 mm to about 0.61 mm, particularly about 0.15 mm, about 0.25 mm, or about 0.61 mm.

In certain embodiments, the cannula has an outer diameter in the range from about 0.31 mm to about 0.91 mm, particularly about 0.31 mm, about 0.52 mm, or about 0.91 mm. It is clear to the skilled person that the inner diameter of the cannula is smaller than the outer diameter of the cannula.

In certain embodiments, the speed of the raw substrate relative to the cannula during the silver composition application step is in the range from about 1 mm/s to about 30 mm/s, particularly in the range from about 2 mm/s to about 15 mm/s, particularly about 8 mm/s or about 10 mm/s.

In certain embodiments, the flow rate of the silver composition during the silver composition application step is in the range from about 0.007 ml/min to about 0.30 ml/min, preferably in the range from about 0.01 ml/min to about 0.03 ml/min, particularly about 0.015 ml/min.

In certain embodiments, the distance between the cannula and the surface of the first side of the raw substrate to which the silver composition is applied during the silver composition application step is in the range from about 20 μm to about 200 μm, preferably in the range from about 50 μm to about 150 μm, particularly about 50 μm.

In certain embodiments, the resulting line thickness of the silver composition applied from the cannula during the silver composition application step is about 0.2 mm to about 1.1 mm, particularly about 0.2 to about 0.3 mm, about 0.4 mm to about 0.5 mm, about 0.5 mm to about 0.6 mm, or about 0.9 mm to about 1.1 mm.

In certain embodiments described herein, as schematically depicted in FIG. 3, in the silver composition application step, a silver composition comprising a counter electrode/reference electrode (CERE) paste may be applied in two steps. The steps can be conducted in different orders or simultaneously. In a first step c1), the CERE paste is applied as a continuous line along the substrate sheet. In a second step c2), short lines are applied along the future sensor. As mentioned above, step c2) can alternatively be carried out prior to step c1). The resulting short lines take the form of "bars" acting later as "storage vessels". In a next step, the whole CERE print is covered by a protection layer using any desired method. During a subsequent sensor separation step, the inner "storage vessel" remains not cut, but the continuous line gets cut and acts as a tunnel for mass transfer between the short line or bar acting as storage vessel and the medium surrounding the sensor once implanted in a host. Clearly, the thickness and width of the "tunnel" must not exceed the threshold value, in order to avoid the black-out effect.

In an embodiment, in the region in which the second silver composition partially overlaps with the first silver composition, the first silver composition region intersects with the second silver composition regions to form a + shape design at each intersection (i.e., the region where they intersect is identical to the overlapping region). Note that as one of ordinary skill in the art would recognize, the design shapes described herein can readily be seen once the sensors are formed in the subsequent cutting step described below. Thus, the short lines or bars can take the form of a + sign design when the short lines are applied over the firstly applied continuous line with each one appearing as a short line extending above and below the continuous line. In other words, the horizontal part of the + sign design is the continuous line, and the vertical part of the + sign design is the short line applied in the separate step. It should be understood that the + shape also encompasses a cross-shaped design where the first and the second silver layers intersect and partially overlap but do not bisect one another.

In another embodiment, in the region in which the second silver composition partially overlaps with the first silver composition, the first silver composition region intersects with the second silver composition regions to form a T shape design at each intersection (i.e., the region where they intersect is identical to the overlapping region). Thus, the short lines or bars can take the form of a T-shape design when the short lines are applied over the firstly applied continuous line with each one appearing as a short line extending either above or below the continuous line. In other words, the horizontal part of the T-shape design is the continuous line, and the vertical part of the T-shape design is the short line applied in the separate step. It should be understood that the T-shape also encompasses a design where the first and the second silver composition regions intersect and partially overlap but wherein the length of the second silver composition region does not extend to the full length of the first silver layer or vice versa.

In other words, the position of the "tunnel" line may be varied relative to the position of the "storage vessel" line. An embodiment of a CERE where the "tunnel" line is disposed at either end of the "storage vessel" is thus denoted as a "T" shape CERE because of its form, whereas disposing the "tunnel" line somewhere in-between the ends of the "storage vessel" is referred to with the notation "+" CERE. Each design has advantages: the "+" form has an advantage of better accessibility of the AgCl in the "storage vessel", while the "T" form allows placing the exposed AgCl areas further away from the sensing layer disposed on the other side of the sensor. The "+" shape allows shorter sensors to provide more AgCl. This has an advantage in providing a more stable reference potential at higher current loadings. All else being equal, as more AgCl is accessible in a sensor and the easier it is to access, the better is the functioning of the CERE.

TABLE 1

| | Exemplary Embodiments of Line Coating Parameters (Horizontal Line ("Tunnel" Line)) | | | | |
| Design | Cannula Size OD [mm] | Cannula Size ID [mm] | Speed [mm/s] | Distance substrate [μm] | Resulting Line Thickness [mm] |
|---|---|---|---|---|---|
| + | 0.31 | 0.15 | 8 | 50 | 0.2-0.3 |
| + | 0.52 | 0.25 | 8 | 50 | 0.5-0.6 |
| + | 0.91 | 0.61 | 8 | 50 | 0.9-1.1 |
| T | 0.31 | 0.15 | 8 | 50 | 0.2-0.3 |
| T | 0.52 | 0.25 | 8 | 50 | 0.5-0.6 |
| T | 0.91 | 0.61 | 8 | 50 | 0.9-1.1 |

TABLE 2

| | | | | | Resulting |
| | Cannula | Cannula | | Distance | Line |
| | Size OD | Size ID | Speed | substrate | Thickness |
| Design | [mm] | [mm] | [mm/s] | [μm] | [mm] |
| --- | --- | --- | --- | --- | --- |
| + | 0.52 | 0.25 | 10 | 50 | 0.4-0.5 |
| T | 0.52 | 0.25 | 10 | 50 | 0.4-0.5 |

Exemplary Embodiments of Line Coating Parameters (Vertical Line (Short Line Acting as Storage Vessel))

In yet another embodiment, in the region in which the second silver composition partially overlaps with the first silver composition, the first silver composition region intersects with the second silver composition regions to form an X shape design at each intersection (i.e., the region where they intersect is identical to the overlapping region). Thus, the short lines or bars can take the form of an X shape design when the short lines are applied over the firstly applied continuous line with each one appearing as a short line extending above and/or below the continuous line. In other words, one part of the X shape design is the continuous line, and the other part of the X shape design is the short line applied in the separate step. It should be understood that the X shape design is constructed in the same way as described above with respect to the T shape design, but wherein the first and second silver composition regions form an acute angle with respect to each other (i.e., the first and second silver composition regions are not perpendicular with respect to each other). It should be understood that this X shape design also encompasses a design wherein the length of the second silver composition region does not extend to the full length of the first silver composition region or vice versa.

In an exemplary embodiment, the CERE paste comprises 16% Vinnol E 15/48 A DEGMBE/PGMEA 2/1 AA-005 (Ag)/P823-15 (AgCl), further details of which are provided in Table 3 herein. The particle size distribution numbers provided in Table 3 denote the portion of particles with diameters smaller than the D value. For example, D10 is defined as the point on a particle size distribution curve below which 10% of the particles fall. In other words, for D10, the numbers provided in Table 3 represent the particle size where the portion of particles with diameters smaller than this particle size is 10%.

As an alternative to the above-described cannula coating, the T, X or +CERE designs can be manufactured via rotary screen printing.

In step d) a polymer composition is applied on top of the second electrode region as another continuous coating completely covering both previously coated layers to form the membrane. For the polymer composition, the embodiments and preferences described above hold true.

In an embodiment, during the inventive process no polymer composition which comprises a hydrophobic polymer is applied to the first side of the substrate.

The polymer composition may be applied on top of the second electrode region by any method known, for example by a wet-coating process. A suitable wet-coating process is for example selected from the group consisting of spin-coating, spray-coating, doctor-blading, printing, dispensing, slot-coating, dip coating and screen printing. After the wet-coating process, the layer of the polymer composition may be further treated. Such treatments are for example drying treatments, curing treatments and/or laser ablation treatments. Such treatments are known as such.

In step e) the raw substrate, the working electrode region, the second electrode region and the membrane are cut, wherein only the first silver composition region of the second electrode region is cut, to obtain the analyte sensor. In other words, the second silver composition region is not cut in step e). The cutting (sensor separation) takes place along a line where only the first silver layer of the second electrode is present. Preferably, the cutting is carried out such that a plurality of exposed areas of the first silver composition region are formed in the separated sensors, with two such exposed areas preferably being formed, typically on the lateral edges of each cut sensor.

The cutting in step e) is carried out such that analyte sensor strips are formed. These strips may correspond to the analyte sensors. It is also possible that, before or after the raw substrate is cut as described above, that the raw substrate is cut at least once along its other dimension.

Preferably in the method for manufacturing an analyte sensor as described herein, the cutting in step e) comprises laser-cutting.

Further process steps may be carried out. For example, in a step f) a flux limiting membrane may be applied.

Thus, in an embodiment of the inventive method the following step f) is carried out:

TABLE 3

| | Particle | Particle | Particle | Particle | Specific Surface Area of Powder Used to | Weight |
| Name | Size D10 [μm] | Size D50 [μm] | Size D90 [μm] | Size D100 [μm] | Formulate the Paste [m²/g] | % of Paste |
| --- | --- | --- | --- | --- | --- | --- |
| AA-005 (Ag) | 1.1 | 3.1 | 7.7 | 22 | 0.7 | 10 |
| P823-15 (AgCl) | 1.4 | 3.7 | 9 | 58 | 2.2 | 35 |

Exemplary Embodiment of CERE Paste

| Abbr. | Name | |
| --- | --- | --- |
| Vinnol E15/48A | Polyvinyl chloride-co-acrylic acid ester (84 w %/16 w %) | 9 |
| DEGMBE | Diethylene glycol monobutyl ether | 23 |
| PGMEA | Propylene glycol methyl ether acetate | 23 | f) applying a flux limiting membrane to the analyte sensor obtained in step e) to obtain a covered analyte sensor.

For the flux limiting membrane, the preferences and embodiments described above hold true. In particular, the flux limiting membrane, preferably the at least one polymeric material comprised in the flux limiting membrane, may for example be applied by a wet-coating process. A suitable wet-coating process is for example selected from the group consisting of spin-coating, spray-coating, doctor-blading, printing, dispensing, slot-coating, dip coating and screen printing.

As a further example, in a step g) a biocompatibility membrane may be applied.

Thus, in an embodiment of the inventive method, the following step g) is carried out:

g) applying a biocompatibility membrane to the analyte sensor obtained in step e).

If step f) is carried out, then the biocompatibility membrane is typically applied to the covered analyte sensor obtained in step f)

Thus, in case step f) is carried out, in an embodiment the following step g) is carried out:

g) applying a biocompatibility membrane to the covered analyte sensor obtained in step f).

For the biocompatibility membrane, the preferences and embodiments described above hold true. In particular, the biocompatibility membrane usually consists of a biocompatible material. Thus, preferably, in step g) a biocompatible material is applied. The biocompatibility membrane, preferably the biocompatible material may be applied by any process known, in particular by a wet-coating process. A suitable wet-coating process is for example selected from the group consisting of spin-coating, spray-coating, doctor-blading, printing, dispensing, slot-coating, dip coating and screen printing.

Another aspect of the present invention is, therefore, also an analyte sensor obtainable by the inventive method for manufacturing an analyte sensor.

A further aspect of the present invention is an analyte sensor system comprising:

the inventive analyte sensor and an electronics unit, the electronics unit being configured to be electronically connected to the analyte sensor.

For the analyte sensor comprised in the analyte sensor system, the embodiments and preferences described above for the inventive analyte sensor hold true.

The term "electronics unit" as used herein is a broad term and is to be given its ordinary and customary meaning to a person of ordinary skill in the art and is not to be limited to a special or customized meaning. The term specifically may refer, without limitation, to a unit, such as a unit which may be handled as a single piece, which is configured for performing at least one electronic function. Specifically, the electronics unit may have at least one interface for being connected to the analyte sensor, wherein the electronics unit may provide at least one electronic function interacting with the analyte sensor, such as at least one measurement function. The electronics unit specifically may be configured for measuring at least one voltage and/or for measuring at least one current, thereby interacting with the analyte sensor. The electronics unit may further comprise at least one integrated circuit, such as a processor and/or a battery. The term "processor" as generally used herein is a broad term and is to be given its ordinary and customary meaning to a person of ordinary skill in the art and is not to be limited to a special or customized meaning. The term specifically may refer, without limitation, to an arbitrary logic circuitry configured for performing basic operations of a computer or system, and/or, generally, to a device which is configured for performing calculations or logic operations. In particular, the processor may be configured for processing an electronic signal, such as a current or a voltage, specifically an electronic signal from the analyte sensor. Specifically, the processor may be or may comprise a microcontroller unit (MCU). Additionally or alternatively, the processor may be or may comprise a microprocessor, thus specifically the processor's elements may be contained in one single integrated circuitry (IC) chip. Additionally or alternatively, the processor may be or may comprise one or more application-specific integrated circuits (ASICs) and/or one or more field-programmable gate arrays (FPGAs) or the like. The processor specifically may be configured, such as by software programming, for performing one or more evaluation operations. Thus, the processor may be configured for processing and/or evaluating the electronic signal from the analyte sensor and, for example, outputting a signal indicating the analyte concentration measured by the analyte sensor. The electronics unit further may comprise at least one measuring device for measuring at least one of a voltage and a current, such as a potentiostat. Further, the electronics unit may comprise a microcontroller, specifically being configured for controlling one or more electronic functions of the electronics unit.

The electronics unit specifically may comprise at least one electronics unit housing, wherein the analyte sensor, e.g. with a proximal end and/or an end providing electrical contacts for contacting the analyte sensor, may protrude into the electronics unit housing and may be electrically connected with at least one electronic component within the electronics unit housing. As an example, the proximal end and/or at least one contact portion of the analyte sensor may protrude into the electronics unit housing and, therein, may be electrically connected to at least one electronic component, such as to at least one printed circuit board and/or at least one contact portion of the electronics unit, e.g. by one or more of a soldering connection, a bonding connection, a plug, a clamping connection or the like. The electronics unit specifically may be used and/or configured as a transmitter for transmitting measurement data to at least one external device, such as to at least one receiver, e.g. wirelessly.

The electronics unit is electronically connected to the analyte sensor. Thus, an electrical connection exists between the analyte sensor and the electronics unit. The electronics unit comprised in the analyte sensor system is in contact with the analyte sensor. For example, the conductive trace and the second conductive trace of the analyte sensor may each form an electrical connection with the electronics unit. Typically, the analyte sensor comprises the contact portion at a proximal end and the working electrode and the second electrode at a distal end. Thus, an electrical signal, such as an electrical current and/or an electric voltage, may be transmitted via the electronic connection from the analyte sensor to the electronics unit. Via the electrical connection, the electronics unit may interact with the analyte sensor for performing at least one electrochemical measurement. The electrical connection specifically, as outlined above, may be established by at least one connection portion of the analyte sensor protruding into a housing of the electronics unit.

DRAWINGS

The embodiments set forth in the drawings are illustrative and exemplary in nature and not intended to limit the inventions defined by the claims. The following detailed description of the illustrative embodiments can be understood when read in conjunction with the following drawings, where like structure is indicated with like reference numerals and in which:

Figure 3:
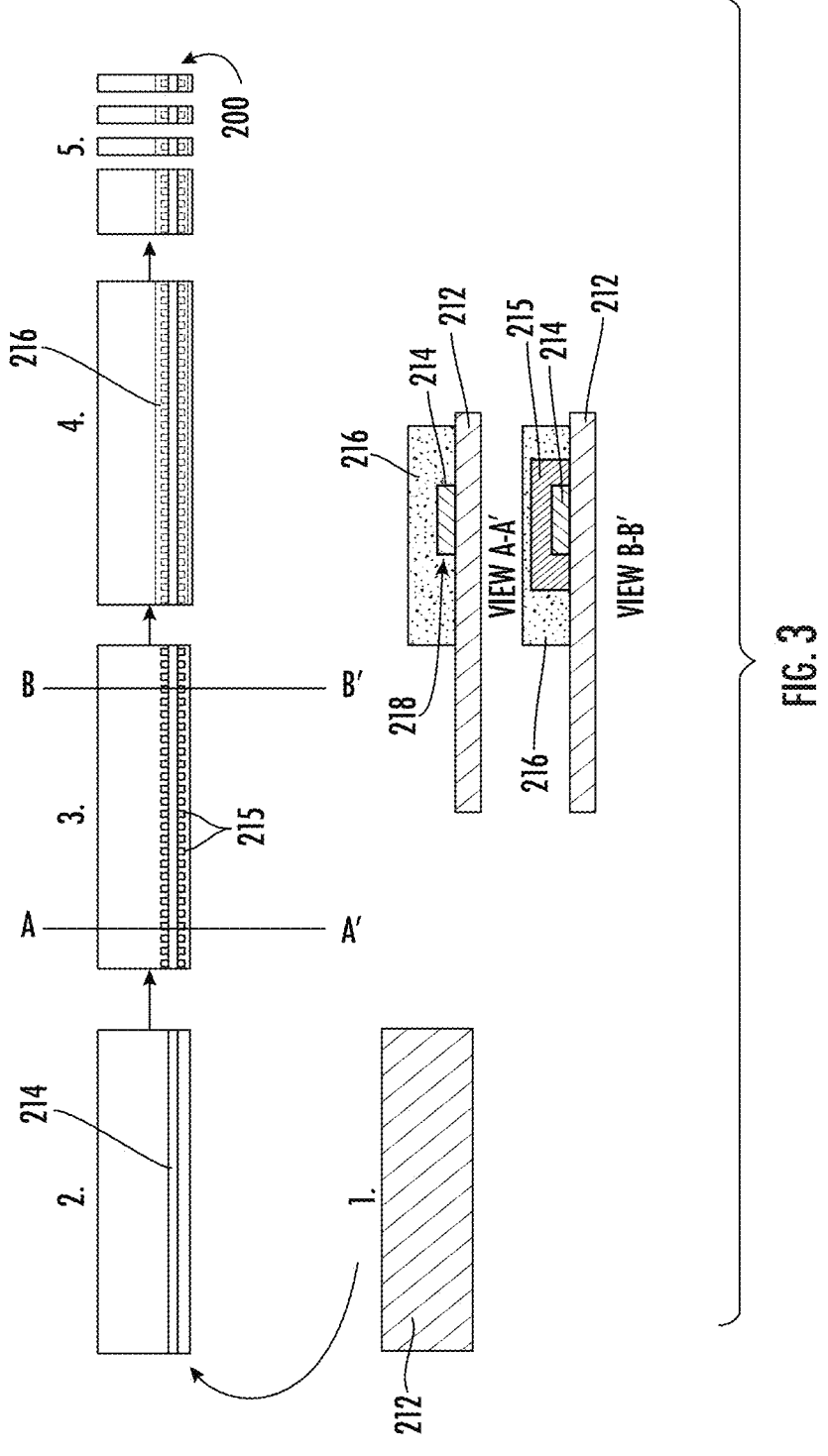

FIG. 3 is a diagram depicting exemplary second electrodes of analyte sensors as disclosed herein and a method for making such sensors, according to one or more embodiments described herein, wherein cross-sections are taken along lines A-A' and B-B' and where such cross-sectional views are also illustrated; and FIGS. 4A-4F are diagrams depicting exemplary second electrode design shapes of analyte sensors as disclosed herein, according to one or more embodiments described herein.

DESCRIPTION

Specific embodiments of the present disclosure will now be described. The invention may, however, be embodied in different forms and should not be construed as limited to the embodiments set forth herein. Rather, these embodiments are provided so that this disclosure will be thorough and complete, and will fully convey the scope of the invention to those skilled in the art.

Unless otherwise defined, all technical and scientific terms used herein have the same meaning as commonly understood by one of ordinary skill in the art to which embodiments of this invention belong. The terminology used herein is for describing particular embodiments only and is not intended to be limiting of the invention. As used in the specification and appended claims, the singular forms "a," "an," and "the" are intended to include the plural forms as well, unless the context clearly indicates otherwise.

Methods and systems and parts thereof described herein can be combined to implement embodiments of the invention.

Figure 1:
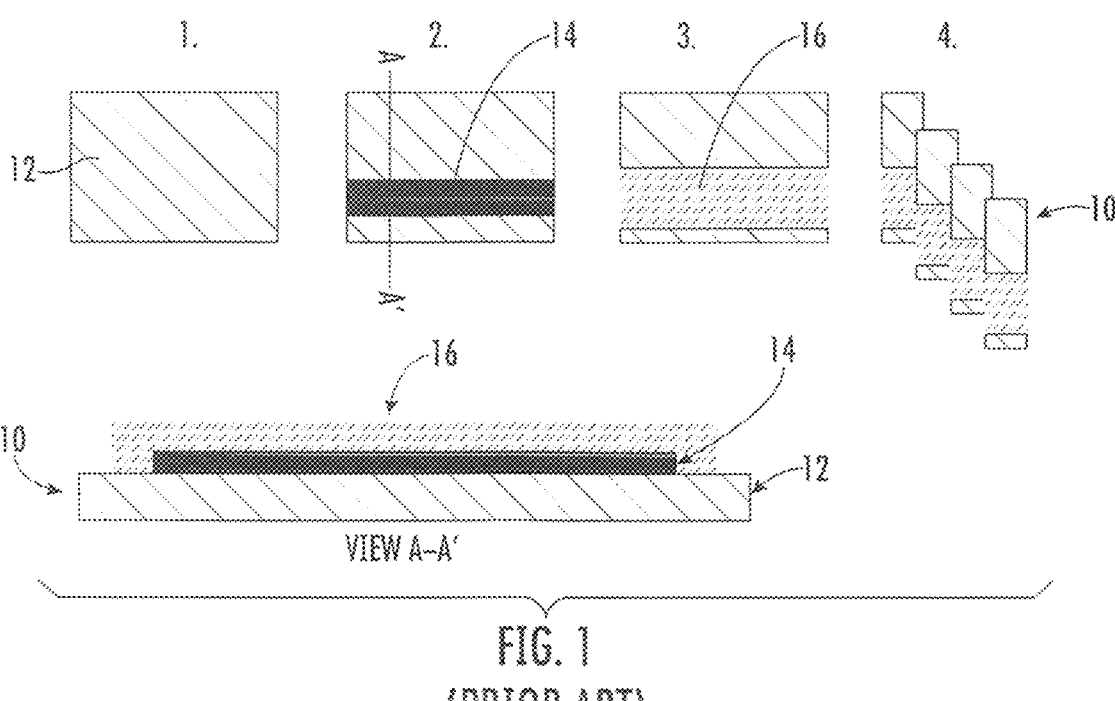
FIG. 1 is a diagram depicting second electrodes of prior art analyte sensors and depicts a method for making such second electrodes of these sensors, wherein a cross-section is taken along lines A-A' and such cross-sectional view is also illustrated (Prior Art)

Referring to FIG. 1 (Prior Art), there is shown a high-level drawing depicting second electrodes of prior art analyte sensors and depicts a method for making such second electrodes of these sensors, wherein a cross-section is taken along lines A-A' and such cross-sectional view is also depicted. In a first step, a raw substrate 12 is provided. In a next step, a second electrode 14, formed from a silver composition, is applied on top of the substrate 12. In the following step, a membrane 16 is applied over the second electrode 14 and part of the substrate 12. In the last step depicted, a number of analyte sensors 10 are depicted and are formed by carrying out a cutting step. In the cross-sectional view, it should be noted that the cross-sectional view is actually a view of the layered construction shown after application of the membrane 16, but the lines A-A' are shown in the earlier process step so that it is clear where the cutting is taking place relative to the second electrode 14.

Figure 2:
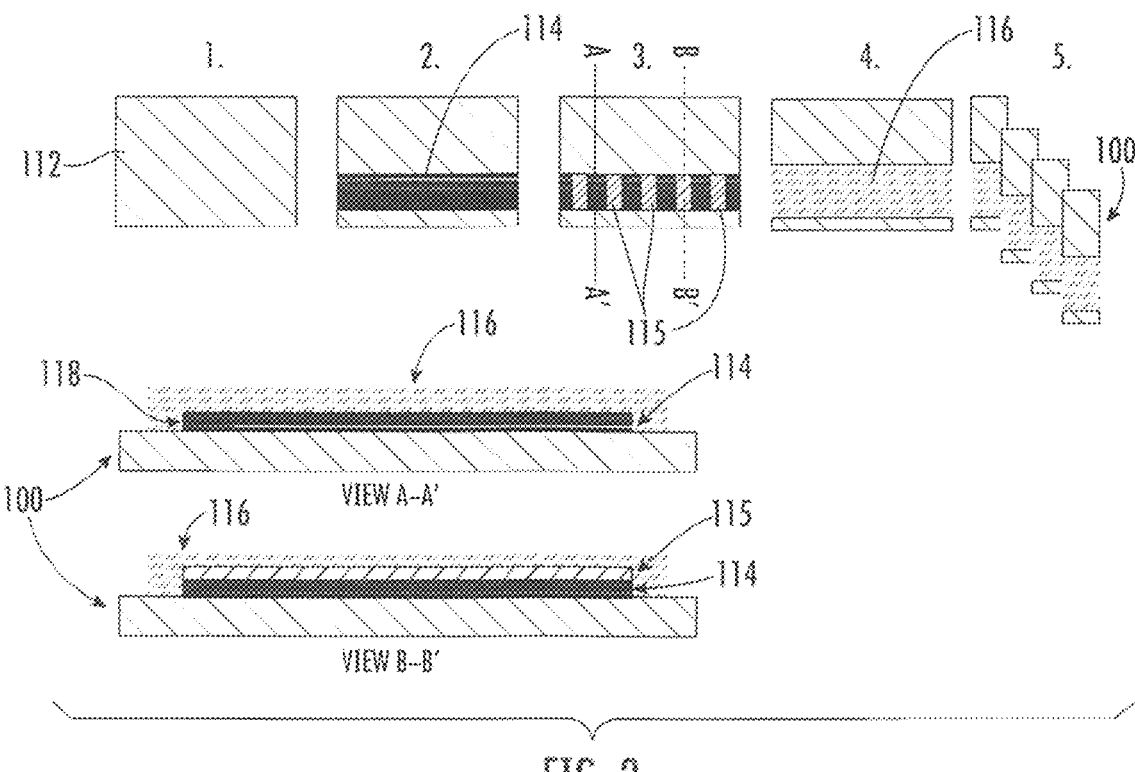
FIG. 2 is a diagram depicting exemplary second electrodes of analyte sensors as disclosed herein and a method for making such sensors, according to one or more embodiments described herein, wherein cross-sections are taken along lines A-A' and B-B' and where such cross-sectional views are also illustrated.

Referring to FIG. 2, a high-level drawing is provided depicting exemplary second electrodes of analyte sensors of embodiments of the invention and depicts a method for making such second electrodes of these sensors, wherein cross-sections are taken along lines A-A' and B-B' and such cross-sectional views are also depicted. In a first step, a raw substrate 112 is provided. In a next step, a first silver layer region 114 is applied on top of the substrate 112. In a next step, at least one second silver layer region 115, and preferably a plurality of second silver layer regions 115, is/are applied on top of the first silver layer region 114 such that the second silver layer region(s) 115 partially overlap with the first silver layer region 114. In the following step, a membrane 116 is applied over the first silver layer region 114 and the second silver layer region(s) 115. The membrane 116 may be applied such that it partially covers areas of the raw substrate 112.

In the last step depicted, a number of analyte sensors 100 are depicted and are formed by carrying out a cutting step. The cutting step is carried out by cutting along the lines A-A'. This area depicted by the lines A-A' is typically cut in each such area to thereby form the sensors 100. As the sensor is cut as shown by the lines A-A', at this sensor edge, the first silver layer is exposed to form at least one exposed area 118 of the first silver layer, said at least one exposed area 118 being disposed on the exterior of the sensor and configured to be in direct contact with body fluid when the sensor is implanted in a user. Preferably, each sensor is manufactured such that it comprises a plurality of the exposed areas 118, and more preferably comprises at least one such exposed area 118 on each lateral side of the sensor. At the sensor edge formed as shown by the lines A-A', the second silver layer is not cut, and thus, the second silver layer is formed in the sensor such that it is not configured to be in direct contact with body fluid when the sensor is implanted in a user. In carrying out the cutting step, it is preferred to cut as shown at the lines A-A' on either side of each of the second silver layer regions 115 to form the sensors.

The main function of the first silver layer is to provide a channel for mass transport between the second silver layer which it partially overlaps with and the body fluid (e.g., interstitial fluid), and may also provide electrical contact between the second silver layer and the conductive substrate. Thus, the first silver layer may comprise no AgCl, but have sufficient Ag. Preferably, though, the first silver layer also comprises some AgCl (typically <30 wt % based on the total weight of the first silver layer) to provide functionality of the second electrode for the time period after implantation in a user until the second silver layer gets penetrated by interstitial fluid and plays its role as a storage vessel of AgCl. Since the first silver layer comprises relatively less or no AgCl, its exposed surface area can be safely increased.

In the cross-sectional views, it should be noted that each cross-sectional view is actually a view of the layered construction shown after application of the membrane 116, but the section lines A-A' and B-B' are shown in the earlier process step so that it is clear where the cutting is taking place relative to the second electrode 114. Thus, the cross-sectional view A-A' depicts a cut edge (a separation line) of a sensor, and the cross-sectional view B-B' depicts merely a cross-sectional view through each sensor where the second silver layer region 115 is located.

It should be noted that the drawings are not drawn to scale, and particularly the cross-sectional views are not drawn to scale. Further, it is understood that the drawings depict only the substrate 112, the components of the second electrode, and the membrane 116 to provide for simplicity and clarity.

Referring to FIG. 3, a high-level drawing is provided depicting exemplary second electrodes of analyte sensors of embodiments of the invention and depicts a method for making such second electrodes of these sensors, wherein cross-sections are taken along lines A-A' and B-B' and such cross-sectional views are also depicted. In a first step, a raw substrate 212 is provided. In a next step, a first silver layer region 214 is applied on top of the substrate 212, and at least one second silver layer region 215, and preferably a plurality of second silver layer regions 215, is/are applied on top of the first silver layer region 214 such that the second silver layer region(s) 215 partially overlap with the first silver layer region 214. In a next step, a membrane 216 is applied over the first silver layer region 214 and the second silver layer region(s) 215. The membrane 216 may be applied such that it partially covers areas of the raw substrate 212.

In the last step depicted, a number of analyte sensors 200 are depicted and are formed by carrying out a cutting step. The cutting step is carried out by cutting along the lines A-A'. This area depicted by the lines A-A' is typically cut in each such area to thereby form the sensors 200. As the sensor is cut as shown by the lines A-A', at this sensor edge, the first silver layer is exposed to form at least one exposed area 218 of the first silver layer, said at least one exposed area 218 being disposed on the exterior of the sensor and configured to be in direct contact with body fluid when the sensor is implanted in a user. Preferably, each sensor is manufactured such that it comprises a plurality of the exposed areas 218, and more preferably comprises at least one such exposed area 218 on each lateral side of the sensor. At the sensor edge formed as shown by the lines A-A', the second silver layer is not cut, and thus, the second silver layer is formed in the sensor such that it is not configured to be in direct contact with body fluid when the sensor is implanted in a user. In carrying out the cutting step, it is preferred to cut as shown at the lines A-A' on either side of each of the second silver layer regions 215 to form the sensors.

The main function of the first silver layer is to provide a channel for mass transport between the second silver layer which it partially overlaps with and the body fluid (e.g., interstitial fluid), and may also provide electrical contact between the second silver layer and the conductive substrate. Thus, the first silver layer may comprise no AgCl, but have sufficient Ag. Preferably, though, the first silver layer also comprises some AgCl (typically <30 wt % based on the total weight of the first silver layer) to provide functionality of the second electrode for the time period after implantation in a user until the second silver layer gets penetrated by interstitial fluid and plays its role as a storage vessel of AgCl. In a particularly preferred embodiment, the first silver layer and the second silver layer have the same compositions.

Referring to FIGS. 4A-4F, various designs for the first and second silver layers of the at least one second electrode of analyte sensors are depicted. The second silver layer intersects with the first silver layer and partially overlaps with the first silver layer to form an overlapping region.

Figures 4A, 4B, 4C, 4D, 4E, 4F:
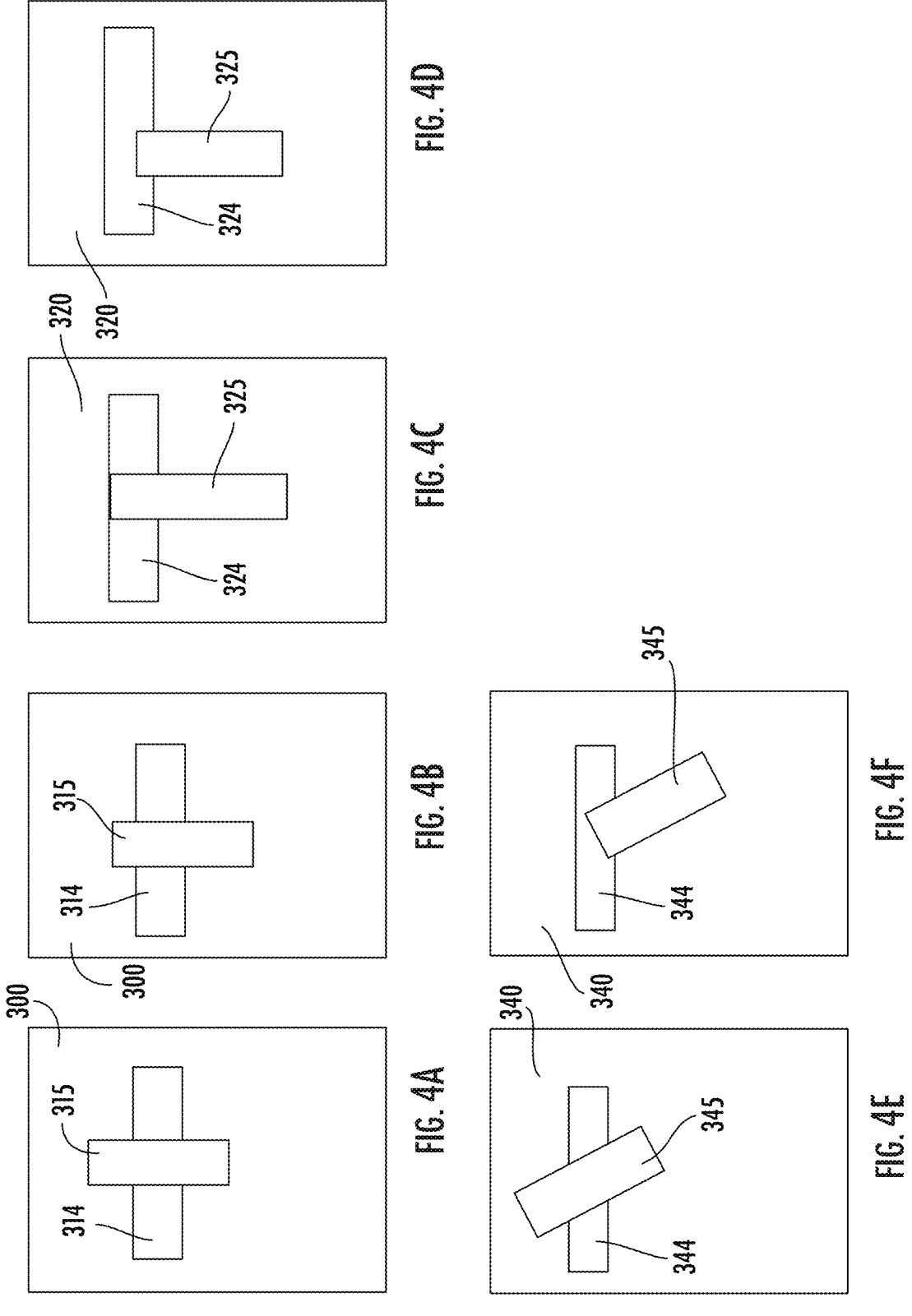

As shown in FIGS. 4A and 4B, in an embodiment, an analyte sensor 300 comprises a first silver layer 314 that intersects with a second silver layer 315 to form a + shape design. Here, it should be understood that the + shape design refers to a configuration of the at least one second electrode wherein the first and second silver layers intersect and partially overlap to form a + shape. It should be understood that the + shape also encompasses a cross-shaped design as depicted in FIG. 4B where the first and the second silver layers intersect and partially overlap but do not bisect one another.

As shown in FIGS. 4C and 4D, in an embodiment, an analyte sensor 320 comprises a first silver layer 324 that intersects with a second silver layer 325 to form a T shape design. Here, it should be understood that the T shape design refers to a configuration of the at least one second electrode wherein the first and second silver layers intersect and partially overlap to form a T shape. It should be understood that the T shape also encompasses a design as depicted in FIG. 4D where the first and the second silver layers intersect and partially overlap but wherein the length of the second silver layer does not extend to the full width of the first silver layer or vice versa.

As shown in FIGS. 4E and 4F, in an embodiment, an analyte sensor 340 comprises a first silver layer 344 that intersects with a second silver layer 345 to form an X shape design. Here, it should be understood that the X shape design refers to a configuration of the at least one second electrode wherein the first and second silver layers intersect and partially overlap to form an X shape. It should be understood that the X shape design is constructed in the same way as described above with respect to the T shape design, but wherein the first and second silver layers form an acute angle with respect to each other (i.e., the first and second silver layers are not perpendicular with respect to each other). It should be understood that this X shape design also encompasses a design as depicted in FIG. 4F wherein the length of the second silver layer does not extend to the full width of the first silver layer or vice versa.

In the cross-sectional views, it should be noted that each cross-sectional view is actually a view of the layered construction shown after application of the membrane 216, but the section lines A-A' and B-B' are shown in the earlier process step so that it is clear where the cutting is taking place relative to the second electrode 214. Thus, the cross-sectional view A-A' depicts a cut edge (a separation line) of a sensor, and the cross-sectional view B-B' depicts merely a cross-sectional view through each sensor where the second silver layer region 215 is located.

It should be noted that the drawings are not drawn to scale, and particularly the cross-sectional views are not drawn to scale. Further, it is understood that the drawings depict only the substrate 212, the components of the second electrode, and the membrane 216 to provide for simplicity and clarity.

Having shown and described various versions in the present disclosure, further adaptations of the methods and systems described herein may be accomplished by appropriate modifications by one of ordinary skill in the art without departing from the scope of the present invention. Several of such potential modifications have been mentioned, and others will be apparent to those skilled in the art.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

REFERENCE SIGNS LIST

10 Analyte sensor (prior art)
12 Raw substrate (prior art)
14 Second electrode (prior art)
16 Membrane (prior art)
100 Analyte sensor 112 Raw substrate
114 First silver layer region
115 Second silver layer region(s)
116 Membrane
118 Exposed area of the first silver layer
200 Analyte sensor
212 Raw substrate
214 First silver layer region
215 Second silver layer region(s)
216 Membrane
218 Exposed area of the first silver layer
300 Analyte sensor
314 First silver layer region
315 Second silver layer region(s)
320 Analyte sensor
324 First silver layer region
325 Second silver layer region(s)
340 Analyte sensor
344 First silver layer region
345 Second silver layer region(s)

What is claimed is:

1. An analyte sensor comprising
a substrate comprising a first side and a second side;
at least one working electrode positioned on the first side of the substrate, the at least one working electrode comprising at least one electrically conductive material;
at least one second electrode positioned on the second side of the substrate, the at least one second electrode comprising at least one first silver layer and at least one second silver layer, wherein the at least one second silver layer partially overlaps with the at least one first silver layer, wherein the at least one first and second silver layers comprise the same composition; and
a membrane comprising a polymer composition which comprises a hydrophobic polymer, wherein the membrane is located on top of the at least one second electrode,
wherein the analyte sensor comprises at least one exposed area of the at least one first silver layer, said at least one exposed area being disposed on an exterior of the analyte sensor and configured to be in direct contact with body fluid when the analyte sensor is implanted in a user.

2. The analyte sensor according to claim 1, wherein the at least one first silver layer intersects with the at least one second silver layer to form a + shape design.

3. The analyte sensor according to claim 1, wherein the at least one first silver layer intersects with the at least one second silver layer to form a T shape design.

4. The analyte sensor according to claim 1, wherein the at least one first silver layer intersects with the at least one second silver layer to form an X shape design.

5. The analyte sensor according to claim 1, wherein the analyte sensor is an implantable sensor.

6. The analyte sensor according to claim 1, wherein the at least one second electrode is selected from the group consisting of a counter electrode, a reference electrode and a combined counter/reference electrode.

7. The analyte sensor according to claim 1, wherein the first side and the second side of the substrate are positioned opposite each other.

8. The analyte sensor according to claim 1, wherein the at least one second electrode comprises Ag and/or AgCl.

9. The analyte sensor according to claim 1 wherein each of the at least one first and second silver layers comprises in the range from 50 to 99 wt.-% of Ag, in the range from 0 to 30 wt.-% of AgCl and in the range from 1 to 20 wt.-% of a binder based on dry layer weight percentages of a total weight of the respective silver layer.

10. The analyte sensor according to claim 1 wherein each of the at least one first and second silver layers comprises in the range from greater than 0 to less than 59 wt.-% of Ag, in the range from 40 to 99 wt.-% of AgCl, and in the range from 1 to 20 wt.-% of a binder based on dry layer weight percentages of a total weight of the respective silver layer.

11. The analyte sensor according to claim 1, wherein the at least one second electrode comprises AgCl having a load in the range from 20 µg to 150 µg.

12. The analyte sensor according to claim 1, wherein the analyte sensor comprises two of the exposed areas.

13. The analyte sensor according to claim 1, wherein the at least one second silver layer is disposed only on an interior of the analyte sensor and is not disposed on the exterior of the analyte sensor and is not configured to be in direct contact with body fluid when the analyte sensor is implanted in a user.

14. An analyte sensor system comprising
the analyte sensor according to claim 1; and
an electronics unit, the electronics unit being configured to be electronically connected to the analyte sensor.

15. A method for manufacturing an analyte sensor, the method comprising the steps:
a) providing a raw substrate which comprises a first side and a second side;
b) preparing a working electrode region on the first side of the raw substrate, the preparing of the working electrode region comprising the steps:
b1) applying an electrically conductive material to the first side of the raw substrate,
b2) applying a sensing material at least partially on the electrically conductive material;
c) preparing a second electrode region on the second side of the raw substrate, the preparing of the second electrode region comprising the steps:
c1) applying a first silver composition to form a first silver composition region which is essentially continuous on the second side of the raw substrate,
c2) applying a second silver composition as a plurality of separated second silver composition regions on the second side of the raw substrate, wherein the second silver composition has the same composition as the first silver composition and wherein the second silver composition is applied over the first silver composition such that the second silver composition regions partially overlap with the first silver composition region or the first silver composition is applied over the second silver composition so that the first silver composition region partially overlaps with the second silver composition regions;
d) applying a polymer composition on top of the second electrode region, to obtain a membrane, wherein the polymer composition comprises a hydrophobic polymer; and
e) cutting the raw substrate, the working electrode region, the second electrode region and the membrane, wherein only the first silver composition region of the second electrode region is cut such that the first silver composition region comprises at least one exposed area configured to be in direct contact with body fluid when the analyte sensor is implanted in a user.

16. The method according to claim 15, wherein in the regions in which the second silver composition partially overlaps with the first silver composition, the first silver composition region intersects with the second silver composition regions to form a + shape design at each intersection.

17. The method according to claim 15, wherein in the regions in which the second silver composition partially overlaps with the first silver composition, the first silver composition region intersects with the second silver composition regions to form a T shape design at each intersection.

18. The method according to claim 15, wherein in the regions in which the second silver composition partially overlaps with the first silver composition, the first silver composition region intersects with the second silver composition regions to form an X shape design at each intersection.

19. The method according to any one of claims 15 to 18, wherein the cutting in step e) comprises cutting such that a plurality of the exposed areas of the first silver composition region are formed.

* * * * *